(12) United States Patent
Pecot et al.

(10) Patent No.: US 10,619,159 B2
(45) Date of Patent: Apr. 14, 2020

(54) METHODS AND COMPOSITIONS USING RNA INTERFERENCE FOR INHIBITION OF KRAS

(71) Applicant: The University of North Carolina at Chapel Hill, Chapel Hill, NC (US)

(72) Inventors: Chad Pecot, Pittsboro, NC (US); Adrienne Cox, Chapel Hill, NC (US); Channing Der, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/070,600

(22) PCT Filed: Jan. 19, 2017

(86) PCT No.: PCT/US2017/014013
§ 371 (c)(1),
(2) Date: Jul. 17, 2018

(87) PCT Pub. No.: WO2017/127473
PCT Pub. Date: Jul. 27, 2017

(65) Prior Publication Data
US 2019/0055562 A1 Feb. 21, 2019

(51) Int. Cl.
| | |
|---|---|
| *C12N 15/113* | (2010.01) |
| *A61K 31/713* | (2006.01) |
| *A61K 9/107* | (2006.01) |
| *A61K 9/127* | (2006.01) |
| *A61P 35/00* | (2006.01) |

(52) U.S. Cl.
CPC ........ *C12N 15/1135* (2013.01); *A61K 9/1075* (2013.01); *A61K 31/713* (2013.01); *A61P 35/00* (2018.01); *C12N 2310/111* (2013.01); *C12N 2310/122* (2013.01); *C12N 2310/14* (2013.01); *C12N 2310/531* (2013.01); *C12N 2320/32* (2013.01)

(58) Field of Classification Search
None
See application file for complete search history.

(56) References Cited

U.S. PATENT DOCUMENTS

2015/0307885 A1 10/2015 Rao et al.

FOREIGN PATENT DOCUMENTS

| WO | 2010/001325 | 1/2010 |
|---|---|---|
| WO | 2010/115206 A2 | 10/2010 |
| WO | 2012/138739 | 10/2012 |
| WO | 2012/171015 | 12/2012 |

OTHER PUBLICATIONS

Cox et al. "Drugging the undruggable Ras: missing possible?", Nat Rev Drug Discov., 13(11):828-851 (2014).
Rachagani et al., "Clinical implications of miRNAs in the pathogenesis, diagnosis and therapy of pancreatic cancer", Adv Drug Deliv Rev., 81:16-33 (2015).
Notification of Transmittal of the International Search Report and the Written Opinion of the International Searching Authority, or the Declaration corresponding to International Application No. PCT/US2017/014013 dated May 4, 2017.
International Preliminary Report on Patentability corresponding to International Application No. PCT/US2017/014013 dated Aug. 2, 2013.
Extended European Search Report corresponding to European Application No. 17741876.1 dated Aug. 16, 2019.
Lin et al. "KRAS Mutation is a Predictor of Oxaliplatin Sensitivity in Colon Cancer Cells", PLOS One 7(11):e50701 (2012) 11 pages.

*Primary Examiner* — Tracy Vivlemore
(74) *Attorney, Agent, or Firm* — Myers Bigel, P.A.

(57) ABSTRACT

The invention relates to the inhibition of expression of mutant KRAS sequences using RNA interference.

20 Claims, 6 Drawing Sheets
Specification includes a Sequence Listing.

FIG. 1

| | CODON 12 13 | | SEQ ID NO: |
|---|---|---|---|
| KRAS GENE: | | | |
| WILD-TYPE | ACTGAATATAAACTTGTGGTAGTTGGAGCT GGT GGC GTAGGCAAGAGTGCCTTGACGATACAG | | 40 |
| G12C MUT | ACTGAATATAAACTTGTGGTAGTTGGAGCT TGT GGC GTAGGCAAGAGTGCCTTGACGATACAG | | 41 |
| G12D MUT | ACTGAATATAAACTTGTGGTAGTTGGAGCT GAT GGC GTAGGCAAGAGTGCCTTGACGATACAG | | 42 |
| G12V MUT | ACTGAATATAAACTTGTGGTAGTTGGAGCT GTT GGC GTAGGCAAGAGTGCCTTGACGATACAG | | 43 |
| G13D MUT | ACTGAATATAAACTTGTGGTAGTTGGAGCT GGT GAC GTAGGCAAGAGTGCCTTGACGATACAG | | 44 |
| siRNA: | | | |
| G12C | ACUGAAUAUAAACUUGUGGUAGUUGGAGCU UGU GGC GUAGGCAAGAGUGCCUUGACGAUACAG | | 45 |
| G12D | ACUGAAUAUAAACUUGUGGUAGUUGGAGCU GAU GGC GUAGGCAAGAGUGCCUUGACGAUACAG | | 46 |
| 12CD13D_1 | ACUGAAUAUAAACUUGUGGUAGUUGGAGCU UGU ACG GUAGGCAAGAGUGCCUUGACGAUACAG | | 47 |
| 12CD13D_2 | ACUGAAUAUAAACUUGUGGUAGUUGGAGCU UAU GAC GUAGGCAAGAGUGCCUUGACGAUACAG | | 47 |
| 12CD13D_3 | ACUGAAUAUAAACUUGUGGUAGUUGGAGCU UAU GAC GUAGGCAAGAGUGCCUUGACGAUACAG | | 47 |
| 12CD13D_4 | ACUGAAUAUAAACUUGUGGUAGUUGGAGCU UAU GAC GUAGGCAAGAGUGCCUUGACGAUACAG | | 47 |
| 12CV13D_1 | ACUGAAUAUAAACUUGUGGUAGUUGGAGCU UUU GAC GUAGGCAAGAGUGCCUUGACGAUACAG | | 48 |
| 12CV13D_2 | ACUGAAUAUAAACUUGUGGUAGUUGGAGCU UUU GAC GUAGGCAAGAGUGCCUUGACGAUACAG | | 48 |

| CONTROL siRNA: | | |
|---|---|---|
| NC | UUCUCCGAACGUGUCACGU | 49 |
| SEQ2 | GUCUCUUGGAUAUUCUCGA | 50 |
| SEQ3 | CAGCUAAUUCAGAAUCAUU | 51 |

| | CODON 12 13 | | SEQ ID NO: |
|---|---|---|---|
| CUSTOM siRNA (TESTED): | | | |
| G12C | ACUGAAUAUAAACUUGUGGUAGUUGGAGCUU*GU*GGCGUAGGCAAGAGUGCCUUGACGAUACAG | | 45 |
| G12D | ACUGAAUAUAAACUUGUGGUAGUUGGAGCUG*AU*GGCGUAGGCAAGAGUGCCUUGACGAUACAG | | 46 |
| 12CD13D_1 | ACUGAAUAUAAACUUGUGGUAGUUGGAGCUU*AU*GACGUAGGCAAGAGUGCCUUGACGAUACAG | | 47 |
| 12CD13D_2 | ACUGAAUAUAAACUUGUGGUAGUUGGAGCUU*AU*GACGUAGGCAAGAGUGCCUUGACGAUACAG | | 47 |
| 12CD13D_3 | ACUGAAUAUAAACUUGUGGUAGUUGGAGCUU*AU*GACGUAGGCAAGAGUGCCUUGACGAUACAG | | 47 |
| 12CD13D_4 | ACUGAAUAUAAACUUGUGGUAGUUGGAGCUU*AU*GACGUAGGCAAGAGUGCCUUGACGAUACAG | | 47 |
| 12CV13D_1 | ACUGAAUAUAAACUUGUGGUAGUUGGAGCUU*UU*GACGUAGGCAAGAGUGCCUUGACGAUACAG | | 48 |
| 12CV13D_2 | ACUGAAUAUAAACUUGUGGUAGUUGGAGCUU*UU*GACGUAGGCAAGAGUGCCUUGACGAUACAG | | 48 |
| SEQUENCES IN BETWEEN CUSTOM siRNAs: | | | |
| 12CD13D_A | ACUGAAUAUAAACUUGUGGUAGUUGGAGCUU*AU*GACGUAGGCAAGAGUGCCUUGACGAUACAG | | 47 |
| 12CD13D_B | ACUGAAUAUAAACUUGUGGUAGUUGGAGCUU*AU*GACGUAGGCAAGAGUGCCUUGACGAUACAG | | 47 |
| 12CD13D_C | ACUGAAUAUAAACUUGUGGUAGUUGGAGCUU*AU*GACGUAGGCAAGAGUGCCUUGACGAUACAG | | 47 |
| 12CD13D_D | ACUGAAUAUAAACUUGUGGUAGUUGGAGCUU*AU*GACGUAGGCAAGAGUGCCUUGACGAUACAG | | 47 |
| 12CD13D_E | ACUGAAUAUAAACUUGUGGUAGUUGGAGCUU*AU*GACGUAGGCAAGAGUGCCUUGACGAUACAG | | 47 |
| 12CD13D_F | ACUGAAUAUAAACUUGUGGUAGUUGGAGCUU*AU*GACGUAGGCAAGAGUGCCUUGACGAUACAG | | 47 |
| CONTROL siRNA: | | | |
| NC | UUCUCCGAACGUGUCACGU | | 49 |
| SEQ2 | GUCUCUUGGAUAUUCUCGA | | 50 |
| SEQ3 | CAGCUAAUUCAGAAUCAUU | | 51 |

*FIG. 4*

SEQUENCE LISTING

```
<160> NUMBER OF SEQ ID NOS: 51

<210> SEQ ID NO 1
<211> LENGTH: 19
<212> TYPE: RNA
<213> ORGANISM: Artificial
<220> FEATURE:
<223> OTHER INFORMATION: siRNA sequence

<400> SEQUENCE: 1
gagcuuauga cguaggcaa
```

```
<210> SEQ ID NO 2
<211> LENGTH: 19
<212> TYPE: RNA
<213> ORGANISM: Artificial
<220> FEATURE:
<223> OTHER INFORMATION: siRNA sequence

<400> SEQUENCE: 2
aguuggagcu uaugacgua                                                 19

<210> SEQ ID NO 3
<211> LENGTH: 19
<212> TYPE: RNA
<213> ORGANISM: Artificial
<220> FEATURE:
<223> OTHER INFORMATION: siRNA sequence

<400> SEQUENCE: 3
gguaguugga gcuuaugac                                                 19

<210> SEQ ID NO 4
<211> LENGTH: 19
<212> TYPE: RNA
<213> ORGANISM: Artificial
<220> FEATURE:
<223> OTHER INFORMATION: siRNA sequence

<400> SEQUENCE: 4
guaguuggag cuuaugacg                                                 19

<210> SEQ ID NO 5
<211> LENGTH: 19
<212> TYPE: RNA
<213> ORGANISM: Artificial
<220> FEATURE:
<223> OTHER INFORMATION: siRNA sequence

<400> SEQUENCE: 5
uaguuggagc uuaugacgu                                                 19

<210> SEQ ID NO 6
<211> LENGTH: 19
<212> TYPE: RNA
<213> ORGANISM: Artificial
<220> FEATURE:
<223> OTHER INFORMATION: siRNA sequence

<400> SEQUENCE: 6
guuggagcuu augacguag                                                 19

<210> SEQ ID NO 7
<211> LENGTH: 19
<212> TYPE: RNA
<213> ORGANISM: Artificial
<220> FEATURE:
<223> OTHER INFORMATION: siRNA sequence

<400> SEQUENCE: 7
uuggagcuua ugacguagg                                                 19

<210> SEQ ID NO 8
<211> LENGTH: 19
<212> TYPE: RNA
<213> ORGANISM: Artificial
<220> FEATURE:
<223> OTHER INFORMATION: siRNA sequence
```

```
<400> SEQUENCE: 8
uggagcuuau gacguaggc                                            19

<210> SEQ ID NO 9
<211> LENGTH: 19
<212> TYPE: RNA
<213> ORGANISM: Artificial
<220> FEATURE:
<223> OTHER INFORMATION: siRNA sequence

<400> SEQUENCE: 9
ggagcuuaug acguaggca                                            19

<210> SEQ ID NO 10
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 10
gagcuuauga cguaggcaan n                                         21

<210> SEQ ID NO 11
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 11
aguuggagcu uaugacguan n                                         21

<210> SEQ ID NO 12
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 12
gguaguugga gcuuaugacn n                                         21

<210> SEQ ID NO 13
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 13
```
guaguuggag cuuaugacgn n         21

<210> SEQ ID NO 14
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 14
uaguuggagc uuaugacgun n         21

<210> SEQ ID NO 15
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 15
guuggagcuu augacguagn n         21

<210> SEQ ID NO 16
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 16
uuggagcuua ugacguaggn n         21

<210> SEQ ID NO 17
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 17
uggagcuuau gacguaggcn n         21

<210> SEQ ID NO 18
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 18

```
ggagcuuaug acguaggcan n                                              21

<210> SEQ ID NO 19
<211> LENGTH: 19
<212> TYPE: RNA
<213> ORGANISM: Artificial
<220> FEATURE:
<223> OTHER INFORMATION: siRNA sequence

<400> SEQUENCE: 19
uugccuacgu cauaagcuc                                                 19

<210> SEQ ID NO 20
<211> LENGTH: 19
<212> TYPE: RNA
<213> ORGANISM: Artificial
<220> FEATURE:
<223> OTHER INFORMATION: siRNA sequence

<400> SEQUENCE: 20
uacgucauaa gcuccaacu                                                 19

<210> SEQ ID NO 21
<211> LENGTH: 19
<212> TYPE: RNA
<213> ORGANISM: Artificial
<220> FEATURE:
<223> OTHER INFORMATION: siRNA sequence

<400> SEQUENCE: 21
gucauaagcu ccaacuacc                                                 19

<210> SEQ ID NO 22
<211> LENGTH: 19
<212> TYPE: RNA
<213> ORGANISM: Artificial
<220> FEATURE:
<223> OTHER INFORMATION: siRNA sequence

<400> SEQUENCE: 22
cgucauaagc uccaacuac                                                 19

<210> SEQ ID NO 23
<211> LENGTH: 19
<212> TYPE: RNA
<213> ORGANISM: Artificial
<220> FEATURE:
<223> OTHER INFORMATION: siRNA sequence

<400> SEQUENCE: 23
acgucauaag cuccaacua                                                 19

<210> SEQ ID NO 24
<211> LENGTH: 19
<212> TYPE: RNA
<213> ORGANISM: Artificial
<220> FEATURE:
<223> OTHER INFORMATION: siRNA sequence

<400> SEQUENCE: 24
cuacgucaua agcuccaac                                                 19

<210> SEQ ID NO 25
<211> LENGTH: 19
<212> TYPE: RNA
```

```
<213> ORGANISM: Artificial
<220> FEATURE:
<223> OTHER INFORMATION: siRNA sequence

<400> SEQUENCE: 25
ccuacgucau aagcuccaa                                                        19

<210> SEQ ID NO 26
<211> LENGTH: 19
<212> TYPE: RNA
<213> ORGANISM: Artificial
<220> FEATURE:
<223> OTHER INFORMATION: siRNA sequence

<400> SEQUENCE: 26
gccuacguca uaagcucca                                                        19

<210> SEQ ID NO 27
<211> LENGTH: 19
<212> TYPE: RNA
<213> ORGANISM: Artificial
<220> FEATURE:
<223> OTHER INFORMATION: siRNA sequence

<400> SEQUENCE: 27
ugccuacguc auaagcucc                                                        19

<210> SEQ ID NO 28
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 28
uugccuacgu cauaagcucn n                                                     21

<210> SEQ ID NO 29
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 29
uacgucauaa gcuccaacun n                                                     21

<210> SEQ ID NO 30
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 30
gucauaagcu ccaacuaccn n                                                     21
```

<210> SEQ ID NO 31
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 31
cgucauaagc uccaacuacn n                                              21

<210> SEQ ID NO 32
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 32
acgucauaag cuccaacuan n                                              21

<210> SEQ ID NO 33
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 33
cuacgucaua agcuccaacn n                                              21

<210> SEQ ID NO 34
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 34
ccuacgucau aagcuccaan n                                              21

<210> SEQ ID NO 35
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 35

```
gccuacguca uaagcuccan n                                              21

<210> SEQ ID NO 36
<211> LENGTH: 21
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (20)..(21)
<223> OTHER INFORMATION: n is dT

<400> SEQUENCE: 36
ugccuacguc auaagcuccn n                                              21

<210> SEQ ID NO 37
<211> LENGTH: 63
<212> TYPE: DNA
<213> ORGANISM: Artificial
<220> FEATURE:
<223> OTHER INFORMATION: Mutated human KRAS gene sequence

<400> SEQUENCE: 37
actgaatata aacttgtggt agttggagct tatgacgtag gcaagagtgc cttgacgata    60
cag                                                                  63

<210> SEQ ID NO 38
<211> LENGTH: 63
<212> TYPE: DNA
<213> ORGANISM: Artificial
<220> FEATURE:
<223> OTHER INFORMATION: Mutated human KRAS gene sequence

<400> SEQUENCE: 38
actgaatata aacttgtggt agttggagct tttgacgtag gcaagagtgc cttgacgata    60
cag                                                                  63

<210> SEQ ID NO 39
<211> LENGTH: 63
<212> TYPE: DNA
<213> ORGANISM: Artificial
<220> FEATURE:
<223> OTHER INFORMATION: Mutated human KRAS gene sequence

<400> SEQUENCE: 39
actgaatata aacttgtggt agttggagct ggtggcgtag gcaagagtgc cttgacgata    60
cag                                                                  63

<210> SEQ ID NO 40
<211> LENGTH: 63
<212> TYPE: DNA
<213> ORGANISM: Homo sapiens

<400> SEQUENCE: 40
actgaatata aacttgtggt agttggagct ggtggcgtag gcaagagtgc cttgacgata    60
cag                                                                  63

<210> SEQ ID NO 41
<211> LENGTH: 63
<212> TYPE: DNA
<213> ORGANISM: Artificial
<220> FEATURE:
<223> OTHER INFORMATION: Mutated human KRAS gene sequence
```

```
<400> SEQUENCE: 41
actgaatata aacttgtggt agttggagct tgtggcgtag gcaagagtgc cttgacgata      60
cag                                                                    63

<210> SEQ ID NO 42
<211> LENGTH: 63
<212> TYPE: DNA
<213> ORGANISM: Artificial
<220> FEATURE:
<223> OTHER INFORMATION: Mutated human KRAS gene sequence

<400> SEQUENCE: 42
actgaatata aacttgtggt agttggagct gatggcgtag gcaagagtgc cttgacgata      60
cag                                                                    63

<210> SEQ ID NO 43
<211> LENGTH: 63
<212> TYPE: DNA
<213> ORGANISM: Artificial
<220> FEATURE:
<223> OTHER INFORMATION: Mutated human KRAS gene sequence

<400> SEQUENCE: 43
actgaatata aacttgtggt agttggagct gttggcgtag gcaagagtgc cttgacgata      60
cag                                                                    63

<210> SEQ ID NO 44
<211> LENGTH: 63
<212> TYPE: DNA
<213> ORGANISM: Artificial
<220> FEATURE:
<223> OTHER INFORMATION: Mutated human KRAS gene sequence

<400> SEQUENCE: 44
actgaatata aacttgtggt agttggagct ggtgacgtag gcaagagtgc cttgacgata      60
cag                                                                    63

<210> SEQ ID NO 45
<211> LENGTH: 63
<212> TYPE: RNA
<213> ORGANISM: Artificial
<220> FEATURE:
<223> OTHER INFORMATION: Mutated siRNA target sequence
<220> FEATURE:
<221> NAME/KEY: misc_feature
<222> LOCATION: (22)..(40)
<223> OTHER INFORMATION: G12C siRNA target sequence

<400> SEQUENCE: 45
acugaauaua aacuuguggu aguuggagcu uguggcguag gcaagagugc cuugacgaua      60
cag                                                                    63

<210> SEQ ID NO 46
<211> LENGTH: 63
<212> TYPE: RNA
<213> ORGANISM: Artificial
<220> FEATURE:
<223> OTHER INFORMATION: Mutated siRNA target sequence
<220> FEATURE:
<221> NAME/KEY: misc_feature
<222> LOCATION: (22)..(40)
<223> OTHER INFORMATION: G12D siRNA target sequence
```

<400> SEQUENCE: 46
acugaauaua aacuuguggu aguuggagcu gauggcguag gcaagagugc cuugacgaua    60
cag                                                                 63

<210> SEQ ID NO 47
<211> LENGTH: 63
<212> TYPE: RNA
<213> ORGANISM: Artificial
<220> FEATURE:
<223> OTHER INFORMATION: Mutated siRNA target sequence
<220> FEATURE:
<221> NAME/KEY: misc_feature
<222> LOCATION: (18)..(36)
<223> OTHER INFORMATION: 12CD13D_4 siRNA target sequence
<220> FEATURE:
<221> NAME/KEY: misc_feature
<222> LOCATION: (19)..(37)
<223> OTHER INFORMATION: 12CD13D_A target sequence
<220> FEATURE:
<221> NAME/KEY: misc_feature
<222> LOCATION: (20)..(38)
<223> OTHER INFORMATION: 12CD13D_B target sequence
<220> FEATURE:
<221> NAME/KEY: misc_feature
<222> LOCATION: (21)..(39)
<223> OTHER INFORMATION: 12CD13D_2 siRNA target sequence
<220> FEATURE:
<221> NAME/KEY: misc_feature
<222> LOCATION: (22)..(40)
<223> OTHER INFORMATION: 12CD13D_C target sequence
<220> FEATURE:
<221> NAME/KEY: misc_feature
<222> LOCATION: (23)..(41)
<223> OTHER INFORMATION: 12CD13D_D target sequence
<220> FEATURE:
<221> NAME/KEY: misc_feature
<222> LOCATION: (24)..(42)
<223> OTHER INFORMATION: 12CD13D_E target sequence
<220> FEATURE:
<221> NAME/KEY: misc_feature
<222> LOCATION: (25)..(43)
<223> OTHER INFORMATION: 12CD13D_F target sequence
<220> FEATURE:
<221> NAME/KEY: misc_feature
<222> LOCATION: (26)..(44)
<223> OTHER INFORMATION: 12CD13D_1 siRNA target sequence
<220> FEATURE:
<221> NAME/KEY: misc_feature
<222> LOCATION: (28)..(46)
<223> OTHER INFORMATION: 12CD13D_3 siRNA target sequence

<400> SEQUENCE: 47
acugaauaua aacuuguggu aguuggagcu uaugacguag gcaagagugc cuugacgaua    60
cag                                                                 63

<210> SEQ ID NO 48
<211> LENGTH: 63
<212> TYPE: RNA
<213> ORGANISM: Artificial
<220> FEATURE:
<223> OTHER INFORMATION: Mutated siRNA target sequence
<220> FEATURE:
<221> NAME/KEY: misc_feature
<222> LOCATION: (21)..(39)
<223> OTHER INFORMATION: 12CV13D_1 siRNA target sequence
<220> FEATURE:
<221> NAME/KEY: misc_feature
<222> LOCATION: (26)..(44)
<223> OTHER INFORMATION: 12CV13D_2 siRNA target sequence

<400> SEQUENCE: 48
acugaauaua aacuuguggu aguuggagcu uuugacguag gcaagagugc cuugacgaua    60

```
cag                                                              63

<210> SEQ ID NO 49
<211> LENGTH: 19
<212> TYPE: RNA
<213> ORGANISM: Artificial
<220> FEATURE:
<223> OTHER INFORMATION: Negative control siRNA sequence

<400> SEQUENCE: 49
uucuccgaac gugucacgu                                             19

<210> SEQ ID NO 50
<211> LENGTH: 19
<212> TYPE: RNA
<213> ORGANISM: Artificial
<220> FEATURE:
<223> OTHER INFORMATION: Positive control siRNA sequence

<400> SEQUENCE: 50
gucucuugga uauucucga                                             19

<210> SEQ ID NO 51
<211> LENGTH: 19
<212> TYPE: RNA
<213> ORGANISM: Artificial
<220> FEATURE:
<223> OTHER INFORMATION: Positive control siRNA sequence

<400> SEQUENCE: 51
cagcuaauuc agaaucauu                                             19
```

METHODS AND COMPOSITIONS USING RNA INTERFERENCE FOR INHIBITION OF KRAS

STATEMENT OF PRIORITY

This application is a 35 U.S.C. § 371 national phase application of PCT Application PCT/US2017/014013 filed Jan. 19, 2017, which claims the benefit of U.S. Provisional Application Ser. No. 62/280,458, filed Jan. 19, 2016, the entire contents of each of which are incorporated by reference herein in its entirety.

STATEMENT REGARDING ELECTRONIC FILING OF A SEQUENCE LISTING

A Sequence Listing in ASCII text format, submitted under 37 C.F.R. § 1.821, entitled 5470-773_ST25.txt, 13,032 bytes in size, generated on Jul. 12, 2018 and filed via EFS-Web, is provided in lieu of a paper copy. This Sequence Listing is hereby incorporated by reference into the specification for its disclosures.

FIELD OF THE INVENTION

The invention relates to the inhibition of expression of mutant KRAS sequences using RNA interference.

BACKGROUND OF THE INVENTION

Since its discovery in 1982, the RAS family of genes has been characterized as an important class of proto-oncogenes (Cox et al., *Nat. Rev. Drug Discov.* 13:828 (2014)). Through three decades of extensive research, mutational activation of certain RAS genes (KRAS, NRAS, and HRAS) has been implicated in nearly one-third of all cancers (Pecot et al., *Mol. Cancer Ther.* 13:2876 (2014)). In particular, KRAS mutations are observed most frequently, both exclusively and in conjunction with the other RAS isoforms (Cox et al., *Nat. Rev. Drug Discov.* 13:828 (2014)). Yet in spite of efforts to develop inhibitors for this highly prevalent mutation, no strong therapeutic candidates have emerged, thus earning the KRAS gene its reputation as an elusively "undruggable" target.

The RAS genes encode a family of small GTPases that act upon downstream effector proteins to promote cell survival, growth, and proliferation (Khosravi-Far et al., *Cancer Metastasis Rev.* 13:67 (1994)). Proper function of the RAS proteins relies upon activation via a guanine nucleotide exchange factor (GEF) to its active, GTP-bound form as well as membrane association of the RAS-GTP complex, both of which have been proposed as targets for KRAS inhibition. However, due to low efficacy and target specificity of previously proposed therapeutic agents in directly inhibiting KRAS, current measures to target the KRAS, pathway focus predominantly on inhibition of downstream effector proteins (Cox et al., *Nat. Rev. Drug Discov.* 13:828 (2014)). Nevertheless, despite challenges in developing a small molecule to directly down-regulate gene activity, KRAS remains a therapeutically relevant target due to its prevalence as a driving mutation in human cancers.

Advances in RNA interference (RNAi) suggest its potential as an effective means of knocking down KRAS expression. RNAi therapy uses the interaction of an exogenous small interfering RNA (siRNA) and endogenous enzymatic machinery, termed an RNA-induced silencing complex (RISC), to selectively silence specific genes at the mRNA level (Pecot et al., *Nat. Rev. Cancer* 11:59 (2011)). A recent study has revealed the efficacy of RNAi as a well-tolerated therapy for inducing metastatic regression in human cancer patients (Tabernero et al., *Cancer Discov.* 3:406 (2013)). In addition, using nanoliposomes we have recently verified the efficacy of siRNA delivery for knockdown of human KRAS in various lung and colon cancer models, both in vitro and in vivo (Pecot et al., *Mol. Cancer Ther.* 13:2876 (2014)).

However, there remains a lack of target-specificity for mutant KRAS over the wild-type (WT) allele. Despite the oncogenic properties of the mutant allele, WT KRAS is necessary for proper response to extra-cellular inputs that promote viability in non-cancerous cells (Khosravi-Far et al., *Cancer Metastasis Rev.* 13:67 (1994)). As such, there is a need for inhibitors that target mutant KRAS while sparing WT KRAS.

Accordingly, the present invention overcomes the deficiencies in the art by providing compositions and methods using RNA interference for specific inhibition of mutant KRAS sequences.

SUMMARY OF THE INVENTION

The present invention is based on the identification of RNA molecules that inhibit expression of mutant KRAS sequences while sparing expression of WT KRAS. Accordingly, one aspect of the invention relates to a double stranded RNA molecule comprising an antisense strand and a sense strand, wherein the nucleotide sequence of the antisense strand is complementary to a region of the nucleotide sequence of a synthetic human KRAS gene that contains the missense mutations G12C, G12D, and G13D or the missense mutations G12C, G12V, and G13D, the region consisting essentially of about 18 to about 25 consecutive nucleotides; wherein the double stranded RNA molecule inhibits expression of a mutant human KRAS gene comprising one or more of the missense mutations G12C, G12D, G12V, and G13D and minimally inhibits expression of wild-type human KRAS.

Another aspect of the invention relates to a composition, e.g., a pharmaceutical composition, comprising one or more of the RNA molecules of the invention.

A further aspect of the invention relates to a method of inhibiting expression of a mutant human KRAS gene comprising one or more of the missense mutations G12C, G12D, G12V, and G13D in a cell, the method comprising contacting the cell with the RNA molecule of the invention, thereby inhibiting expression of the mutant human KRAS gene in the cell.

An additional aspect of the invention relates to a method of treating cancer in a subject in need thereof, wherein the cancer comprises a mutant human KRAS gene comprising one or more of the missense mutations G12C, G12D, G12V, and G13D, the method comprising delivering to the subject the RNA molecule of the invention, thereby treating cancer in the subject.

Another aspect of the invention relates to the use of the RNA molecules of the invention to inhibit expression of a mutant human KRAS gene comprising one or more of the missense mutations G12C, G12D, G12V, and G13D in a cell and to treat cancer in a subject in need thereof, wherein the cancer comprises a mutant human KRAS gene comprising one or more of the missense mutations G12C, G12D, G12V, and G13D.

These and other aspects of the invention are set forth in more detail in the description of the invention below.

BRIEF DESCRIPTION OF THE DRAWINGS

FIG. 1 shows KRAS siRNA sequences (SEQ ID NOS: 40-51). TMS siRNA sequences were designed to bind the G domain of the human KRAS gene at codons 12 and 13 and target three point mutations (each indicated with an asterisk). Underlining indicates the remaining base pairs targeted by the siRNA (sense). Sequences for G12C and G12D siRNAs were obtained from Fleming et al., Mol. Cancer Res. 3:413 (2005). Positive control siRNAs (Seq2 and Seq3) were obtained from Pecot et al., Mol. Cancer Ther. 13:2876 (2014) and targeted a downstream coding region of the KRAS mRNA.

FIG. 4 shows the library of siRNA sequences (SEQ ID NOS:45-51) used for testing all possible siRNA sequence permutations between the custom siRNA sequences.

DETAILED DESCRIPTION OF THE INVENTION

Figure 2A:
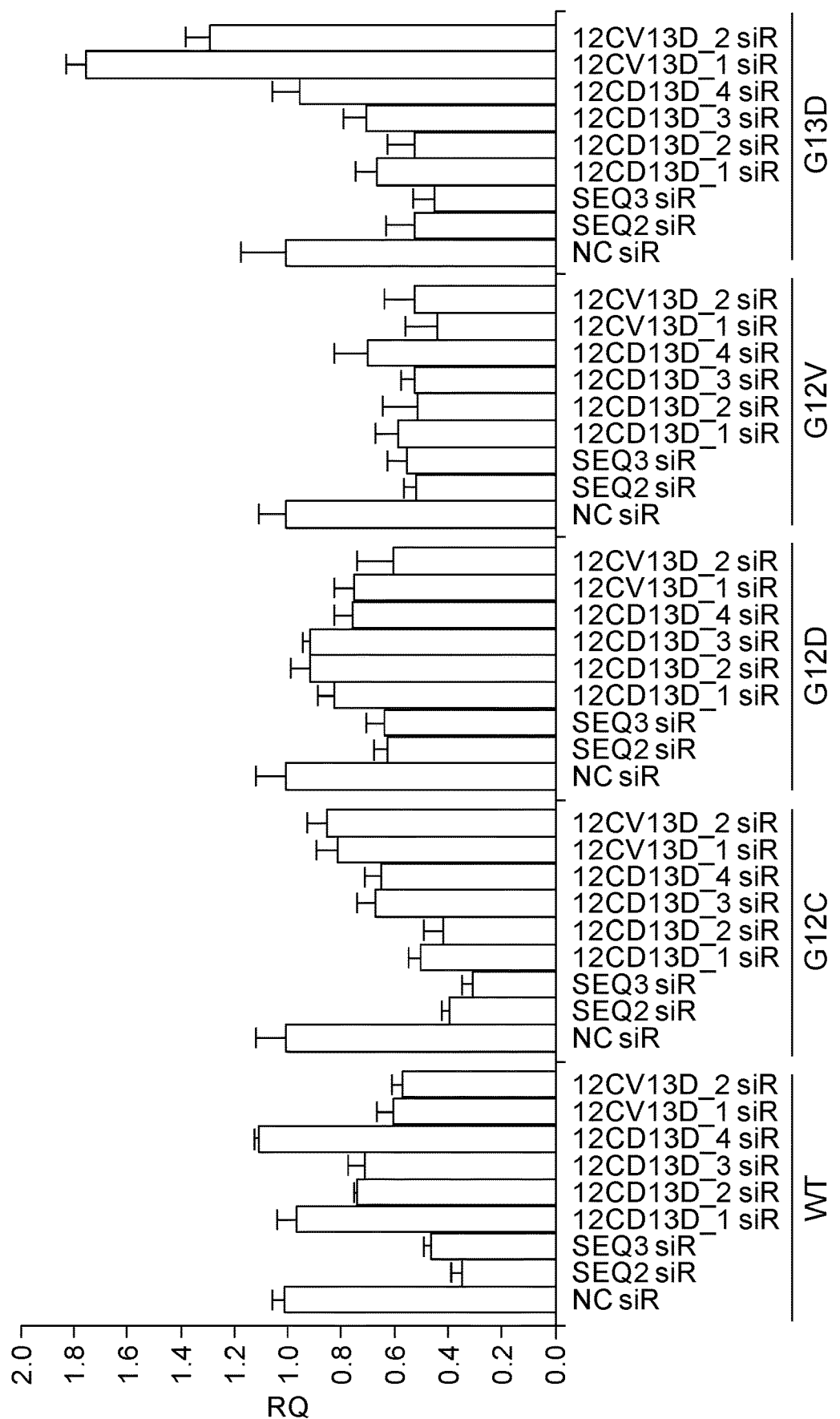
FIGS. 2A-2B show KRAS expression levels with mutant-specific (MS) and control siRNAs. NIH 3T3 cells infected with human WT, G12C, G12D, G12V, or G13D KRAS were reverse transfected with either (A) MS siRNA sequences (12CD13D_1, 12CD13D_2, 12CD13D_3, 12CD13D_4, 12CV13D_1, and 12CV13D_2) or (B) control mutant-specific siRNA or non-specific sequences.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

Definitions

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

As used herein, the transitional phrase "consisting essentially of" (and grammatical variants) is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polynucleotide sequence of this invention, means a polynucleotide that consists of both the recited sequence (e.g., SEQ ID NO) and a total of ten or less (e.g., 1, 2, 3, 4, 5, 6, 7, 8, 9, or 10) additional nucleotides on the 5' and/or 3' ends of the recited sequence such that the function of the polynucleotide is not materially altered. The total of ten or less additional nucleotides includes the total number of additional nucleotides on both ends added together. The term "materially altered," as applied to polynucleotides of the invention, refers to an increase or decrease in ability to inhibit expression of a target mRNA of at least about 50% or more as compared to the expression level of a polynucleotide consisting of the recited sequence.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

A "therapeutically effective" amount as used herein is an amount that provides some improvement or benefit to the subject. Alternatively stated, a "therapeutically effective"

amount is an amount that will provide some alleviation, mitigation, or decrease in at least one clinical symptom in the subject (e.g., in the case of cancer, reduction in tumor burden, prevention of further tumor growth, prevention of metastasis, or increase in survival time). Those skilled in the art will appreciate that the therapeutic effects need not be complete or curative, as long as some benefit is provided to the subject.

By the terms "treat," "treating," or "treatment of," it is intended that the severity of the subject's condition is reduced or at least partially improved or modified and that some alleviation, mitigation or decrease in at least one clinical symptom is achieved.

"Prevent" or "preventing" or "prevention" refer to prevention or delay of the onset of the disorder and/or a decrease in the severity of the disorder in a subject relative to the severity that would develop in the absence of the methods of the invention. The prevention can be complete, e.g., the total absence of cancer in a subject. The prevention can also be partial, such that the occurrence or severity of cancer in a subject is less than that which would have occurred without the present invention.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

An "isolated cell" refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

The term "fragment," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence according to the invention.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and/or adenovirus vectors. Non-viral vectors include, but are not limited to, plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311, filed Mar. 15, 1990).

In some embodiments, a polynucleotide of this invention can be delivered to a cell in vivo by lipofection. Synthetic cationic lipids designed to limit the difficulties and dangers encountered with liposome-mediated transfection can be used to prepare liposomes for in vivo transfection of a nucleotide sequence of this invention (Feigner et al., *Proc. Natl. Acad. Sci. USA* 84:7413 (1987); Mackey, et al., *Proc. Natl. Acad. Sci. U.S.A.* 85:8027 (1988); and Ulmer et al., *Science* 259:1745 (1993)). The use of cationic lipids may promote encapsulation of negatively charged nucleic acids, and also promote fusion with negatively charged cell membranes (Feigner et al., *Science* 337:387 (1989)). Particularly useful lipid compounds and compositions for transfer of nucleic acids are described in International Patent Publications WO95/18863 and WO96/17823, and in U.S. Pat. No. 5,459,127. The use of lipofection to introduce exogenous nucleotide sequences into specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules can be coupled to liposomes chemically.

In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931).

It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

The terms "complementary" or "complementarity," as used herein, refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "substantially complementary" or "partially complementary" mean that two nucleic acid sequences are complementary at least about 50%, 60%, 70%, 80% or 90% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art.

As used herein, "heterologous" refers to a nucleic acid sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g., a different copy number, and/or under the control of different regulatory sequences than that found in nature.

As used herein, the terms "contacting," "introducing" and "administering" are used interchangeably, and refer to a process by which dsRNA of the present invention or a nucleic acid molecule encoding a dsRNA of this invention is delivered to a cell, in order to inhibit or alter or modify expression of a target gene. The dsRNA may be administered in a number of ways, including, but not limited to, direct introduction into a cell (i.e., intracellularly) and/or extracellular introduction into a cavity, interstitial space, or into the circulation of the organism.

"Introducing" in the context of a cell or organism means presenting the nucleic acid molecule to the organism and/or cell in such a manner that the nucleic acid molecule gains access to the interior of a cell. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into cells in a single transformation event or in separate transformation events. Thus, the term "transformation" as used herein refers to the introduction of a heterologous nucleic acid into a cell. Transformation of a cell may be stable or transient.

"Transient transformation" in the context of a polynucleotide means that a polynucleotide is introduced into the cell and does not integrate into the genome of the cell.

By "stably introducing" or "stably introduced" in the context of a polynucleotide introduced into a cell, it is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and mitochondrial genome, and therefore includes integration of the nucleic acid into, for example, the mitochondrial genome. Stable transformation as used herein can also refer to a transgene that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism. Stable transformation of a cell can be detected by, for example, a Northern blot hybridization assay of RNA of the cell with nucleic acid sequences which specifically hybridize with a nucleotide sequence of a transgene introduced into an organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Embodiments of the invention are directed to expression cassettes designed to express the nucleic acids of the present invention. As used herein, "expression cassette" means a nucleic acid molecule having at least a control sequence operably linked to a nucleotide sequence of interest. In this manner, for example, promoters in operable interaction with the nucleotide sequences for the siRNAs of the invention are provided in expression cassettes for expression in an organism or cell.

As used herein, the term "promoter" refers to a region of a nucleotide sequence that incorporates the necessary signals for the efficient expression of a coding sequence. This may include sequences to which an RNA polymerase binds, but is not limited to such sequences and can include regions to which other regulatory proteins bind together with regions involved in the control of protein translation and can also include coding sequences.

Furthermore, a "promoter" of this invention is a promoter capable of initiating transcription in a cell of an organism. Such promoters include those that drive expression of a nucleotide sequence constitutively, those that drive expression when induced, and those that drive expression in a tissue- or developmentally-specific manner, as these various types of promoters are known in the art.

For purposes of the invention, the regulatory regions (i.e., promoters, transcriptional regulatory regions, and translational termination regions) can be native/analogous to the organism or cell and/or the regulatory regions can be native/analogous to the other regulatory regions. Alternatively, the regulatory regions may be heterologous to the organism or cell and/or to each other (i.e., the regulatory regions). Thus, for example, a promoter can be heterologous when it is operably linked to a polynucleotide from a species different from the species from which the polynucleotide was derived. Alternatively, a promoter can also be heterologous to a selected nucleotide sequence if the promoter is from the same/analogous species from which the polynucleotide is derived, but one or both (i.e., promoter and polynucleotide) are substantially modified from their original form and/or genomic locus, or the promoter is not the native promoter for the operably linked polynucleotide.

The choice of promoters to be used depends upon several factors, including, but not limited to, cell- or tissue-specific expression, desired expression level, efficiency, inducibility and selectability. For example, where expression in a specific tissue or organ is desired, a tissue-specific promoter can be used. In contrast, where expression in response to a stimulus is desired, an inducible promoter can be used. Where continuous expression is desired throughout the cells of an organism, a constitutive promoter can be used. It is a routine matter for one of skill in the art to modulate the expression of a nucleotide sequence by appropriately selecting and positioning promoters and other regulatory regions relative to that sequence.

In addition to the promoters described above, the expression cassette also can include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, enhancers, introns, translation leader sequences and polyadenylation signal sequences.

The expression cassette also can optionally include a transcriptional and/or translational termination region (i.e., termination region) that is functional in the organism. A variety of transcriptional terminators are available for use in expression cassettes and are responsible for the termination of transcription beyond the transgene and correct mRNA polyadenylation. The termination region may be native to the transcriptional initiation region, may be native to the operably linked nucleotide sequence of interest, may be native to the host, or may be derived from another source (i.e., foreign or heterologous to the promoter, the nucleotide sequence of interest, the host, or any combination thereof).

A signal sequence can be operably linked to nucleic acids of the present invention to direct the nucleotide sequence into a cellular compartment. In this manner, the expression cassette will comprise a nucleotide sequence encoding the siRNA operably linked to a nucleic acid sequence for the signal sequence. The signal sequence may be operably linked at the N- or C-terminus of the siRNA.

Regardless of the type of regulatory sequence(s) used, they can be operably linked to the nucleotide sequence of the siRNA. As used herein, "operably linked" means that elements of a nucleic acid construct such as an expression cassette are configured so as to perform their usual function. Thus, regulatory or control sequences (e.g., promoters) operably linked to a nucleotide sequence of interest are capable of effecting expression of the nucleotide sequence of interest. The control sequences need not be contiguous with the nucleotide sequence of interest, so long as they function to direct the expression thereof. Thus, for example, intervening untranslated, yet transcribed, sequences can be present between a promoter and a coding sequence, and the promoter sequence can still be considered "operably linked" to the coding sequence. A nucleotide sequence of the present invention (i.e., a siRNA) can be operably linked to a regulatory sequence, thereby allowing its expression in a cell and/or subject.

The expression cassette also can include a nucleotide sequence for a selectable marker, which can be used to select a transformed organism or cell. As used herein, "selectable marker" means a nucleic acid that when expressed imparts a distinct phenotype to the organism or cell expressing the marker and thus allows such transformed organisms or cells to be distinguished from those that do not have the marker. Such a nucleic acid may encode either a selectable or screenable marker, depending on whether the marker confers a trait that can be selected for by chemical means, such as by using a selective agent (e.g., an antibiotic or the like), or on whether the marker is simply a trait that one can identify through observation or testing, such as by screening (Of course, many examples of suitable selectable markers are known in the art and can be used in the expression cassettes described herein.

In some embodiments of the present invention, the expression cassette can comprise an expression control sequence operatively linked to a nucleotide sequence that is a template for one or both strands of the dsRNA. In further embodiments, a promoter can flank either end of the template nucleotide sequence, wherein the promoters drive expression of each individual DNA strand, thereby generating two complementary (or substantially complementary) RNAs that hybridize and form the dsRNA. In alternative embodiments, the nucleotide sequence is transcribed into both strands of the dsRNA on one transcription unit, wherein the sense strand is transcribed from the 5' end of the transcription unit and the antisense strand is transcribed from the 3' end, wherein the two strands are separated by about 3 to about 500 basepairs, and wherein after transcription, the RNA transcript folds on itself to form a short hairpin RNA (shRNA) molecule.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleic acid sequences have at least 60%, 70%, 80% or 90% sequence identity. In some embodiments, the two nucleic acid sequences can have at least 85%, 90%, 95%, 96%, 97%, 98%, 99% or 100% of sequence identity.

An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, J Mol. Biol. 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, Adv. Appl. Math., 2:482-489, 1981, Smith et al., Nucleic Acids Res. 11:2205-2220, 1983).

Useful methods for determining sequence identity are also disclosed in Guide to Huge Computers (Martin J. Bishop, ed., Academic Press, San Diego (1994)), and Carillo, H., and Lipton, D., (Applied Math 48:1073 (1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., J. Mol. Biol. 215:403-410 (1990)); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, "RNAi" or "RNA interference" refers to the process of sequence-specific post-transcriptional gene silencing, mediated by double-stranded RNA (dsRNA). As used herein, "dsRNA" refers to RNA that is partially or completely double stranded. Double stranded RNA is also referred to as small interfering RNA (siRNA), small interfering nucleic acid (siNA), microRNA (miRNA), and the like. In the RNAi process, dsRNA comprising a first (antisense) strand that is complementary to a portion of a target gene and a second (sense) strand that is fully or partially complementary to the first antisense strand is introduced into an organism. After introduction into the organism, the target gene-specific dsRNA is processed into relatively small fragments (siRNAs) and can subsequently become distributed throughout the organism, leading to a loss-of-function mutation having a phenotype that, over the period of a generation, may come to closely resemble the phenotype arising from a complete or partial deletion of the target gene.

MicroRNAs (miRNAs) are non-protein coding RNAs, generally of between about 18 to about 25 nucleotides in length. These miRNAs direct cleavage in trans of target transcripts, negatively regulating the expression of genes involved in various regulation and development pathways (Bartel, Cell, 116:281-297 (2004); Zhang et al. Dev. Biol. 289:3-16 (2006)). As such, miRNAs have been shown to be involved in different aspects of growth and development as well as in signal transduction and protein degradation. Since the first miRNAs were discovered in plants (Reinhart et al. Genes Dev. 16:1616-1626 (2002), Park et al. Curr. Biol. 12:1484-1495 (2002)) many hundreds have been identified. Many microRNA genes (MIR genes) have been identified and made publicly available in a database (miRBase; microrna.sanger.ac.uk/sequences). miRNAs are also described in U.S. Patent Publications 2005/0120415 and 2005/144669A1, the entire contents of which are incorporated by reference herein.

Genes encoding miRNAs yield primary miRNAs (termed a "pri-miRNA") of 70 to 300 bp in length that can form imperfect stemloop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme, Dicer, releasing a miRNA/miRNA* duplex of about 22 nt in size. Many reviews on microRNA biogenesis and function are available, for example, see, Bartel Cell 116:281-297 (2004), Murchison et al. Curr. Opin. Cell Biol. 16:223-229 (2004), Dugas et al. Curr. Opin. Plant Biol. 7:512-520 (2004) and Kim Nature Rev. Mol. Cell Biol. 6:376-385 (2005).

RNA Molecules

The present invention is based on the identification of RNA molecules that inhibit expression of mutant KRAS sequences while sparing expression of WT KRAS. Accordingly, one aspect of the invention relates to a double stranded RNA molecule comprising an antisense strand and a sense strand, wherein the nucleotide sequence of the antisense strand is complementary to a region of the nucleotide sequence of a synthetic human KRAS gene that contains the missense mutations G12C, G12D, and G13D or the missense mutations G12C, G12V, and G13D, the region consisting essentially of about 18 to about 25 consecutive nucleotides; wherein the double stranded RNA molecule inhibits expression of a mutant human KRAS gene comprising one or more of the missense mutations G12C, G12D, G12V, and G13D and minimally inhibits expression of wild-type human KRAS. The region of the KRAS gene targeted by the RNA molecule comprises the nucleotides encoding residues 12 and 13. The RNA molecules provide decreased expression of mutant KRAS in a cell as compared to a wild-type variety of the cell (e.g., a control cell or nontransformed cell). In some embodiments, expression of mutant KRAS is inhibited by at least about 50%, e.g., at least about 50%, 60%, 70%, 80%, 90%, 95%, or more.

A human KRAS gene containing the missense mutations G12C, G12D, and G13D or the missense mutations G12C, G12V, and G13D does not exist in nature. Examples of a region of such artificial gene sequences include SEQ ID NOS:37 and 38, with the mutations relative to the corresponding WT KRAS sequence (SEQ ID NO:39) underlined.

```
                                            SEQ ID NO: 37
ACTGAATATAAACTTGTGGTAGTTGGAGCTTATGACGTAGGCAAGAGTG
CCTTGACGATACAG

SEQ ID NO: 38
ACTGAATATAAACTTGTGGTAGTTGGAGCTTTTGACGTAGGCAAGAGTG
CCTTGACGATACAG
```

-continued

```
                                            SEQ ID NO: 39
ACTGAATATAAACTTGTGGTAGTTGGAGCTGGTGGCGTAGGCAAGAGTG
CCTTGACGATACAG
```

The double stranded RNA molecule can comprise, consist essentially of, or consist of about 18 to about 25 nucleotides (e.g., 18, 19, 20, 21, 22, 23, 24, or 25 or any range therein). Additional nucleotides can be added at the 3' end, the 5' end or both the 3' and 5' ends to facilitate manipulation of the RNA molecule but that do not materially affect the basic characteristics or function of the double stranded RNA molecule in RNA interference (RNAi). Additionally, one or two nucleotides can be deleted from one or both ends of any of the sequences disclosed herein that do not materially affect the basic characteristics or function of the double stranded RNA molecule in RNAi. The term "materially affect" as used herein refers to a change in the ability to inhibit expression of the protein encoded by the mRNA (e.g., WT KRAS) by no more than about 50%, e.g., no more than about 50%, 45%, 40%, 35%, 30%, 25%, 20%, 15%, 10%, or less. Such additional nucleotides can be nucleotides that extend the complementarity of the antisense strand along the target sequence and/or such nucleotides can be nucleotides that facilitate manipulation of the RNA molecule or a nucleic acid molecule encoding the RNA molecule, as would be known to one of skill in the art. For example, a TT overhang at the 3' end may be present, which is used to stabilize the siRNA duplex and does not affect the specificity of the siRNA.

The dsRNA of the invention may optionally comprise a single stranded overhang at either or both ends. The double-stranded structure may be formed by a single self-complementary RNA strand (i.e., forming a hairpin loop) or two complementary RNA strands. RNA duplex formation may be initiated either inside or outside the cell. When the dsRNA of the invention forms a hairpin loop, it may optionally comprise an intron and/or a nucleotide spacer, which is a stretch of nucleotides between the complementary RNA strands, to stabilize the hairpin sequence in cells. The RNA may be introduced in an amount that allows delivery of at least one copy per cell. Higher doses of double-stranded material may yield more effective inhibition.

In particular embodiments, the present invention provides double stranded RNA containing a nucleotide sequence that is fully complementary to a region of the target gene for inhibition. However, it is to be understood that 100% complementarity between the antisense strand of the double stranded RNA molecule and the target sequence is not required to practice the present invention. Thus, sequence variations that might be expected due to genetic mutation, strain polymorphism, or evolutionary divergence can be tolerated. RNA sequences with insertions, deletions, and single point mutations relative to the target sequence may also be effective for inhibition.

In certain embodiments, the nucleotide sequence of the antisense strand contains at least 3 mismatches with the nucleotide sequence of wild-type human KRAS such that the RNA molecule does not target WT KRAS and only minimally inhibits expression of WT KRAS. As used herein, "minimally inhibits expression" means that expression of the protein encoded by the mRNA (e.g., WT KRAS) is inhibited by no more than about 50%, e.g., no more than about 50%, 45%, 40%, 35%, 30%, 25%, 20%, 15%, 10%, or less.

In certain embodiments, the nucleotide sequence of the antisense strand contains no more than 2 mismatches with the nucleotide sequence of a mutant human KRAS gene comprising one or more of the missense mutations G12C, G12D, G12V, and G13D. In some embodiments, the nucleotide sequence of the antisense strand contains at least 3 mismatches with the nucleotide sequence of wild-type human KRAS and contains no more than 2 mismatches with the nucleotide sequence of a mutant human KRAS gene comprising one or more of the missense mutations G12C, G12D, G12V, and G13D.

In some embodiments, the nucleotide sequence of the sense strand comprises a nucleotide sequence that is at least about 80% identical to the nucleotide sequence of any of SEQ ID NOS:1-9, e.g., at least about 80%, 85%, 90%, 91%, 92%, 93%, 94%, 95%, 96%, 97%, 98%, 99%, or more identical to the nucleotide sequence of any of SEQ ID NOS:1-9. In some embodiments, the nucleotide sequence of the sense strand comprises, consists essentially of, or consist of the nucleotide sequence of any of SEQ ID NOS:1-9.

```
                                             SEQ ID NO: 1
GAGCUUAUGACGUAGGCAA

SEQ ID NO: 2
AGUUGGAGCUUAUGACGUA

SEQ ID NO: 3
GGUAGUUGGAGCUUAUGAC

SEQ ID NO: 4
GUAGUUGGAGCUUAUGACG

SEQ ID NO: 5
UAGUUGGAGCUUAUGACGU

SEQ ID NO: 6
GUUGGAGCUUAUGACGUAG

SEQ ID NO: 7
UUGGAGCUUAUGACGUAGG

SEQ ID NO: 8
UGGAGCUUAUGACGUAGGC

SEQ ID NO: 9
GGAGCUUAUGACGUAGGCA
```

In some embodiments, the nucleotide sequence of the antisense strand comprises a nucleotide sequence that is at least about 80% identical to the nucleotide sequence of any of SEQ ID NOS:19-27, e.g., at least about 80%, 85%, 90%, 91%, 92%, 93%, 94%, 95%, 96%, 97%, 98%, 99%, or more identical to the nucleotide sequence of any of SEQ ID NOS: 19-27. In some embodiments, the nucleotide sequence of the antisense strand comprises, consists essentially of, or consist of the nucleotide sequence of any of SEQ ID NOS: 19-27.

```
                                            SEQ ID NO: 19
UUGCCUACGUCAUAAGCUC

SEQ ID NO: 20
UACGUCAUAAGCUCCAACU

SEQ ID NO: 21
GUCAUAAGCUCCAACUACC

SEQ ID NO: 22
CGUCAUAAGCUCCAACUAC

SEQ ID NO: 23
ACGUCAUAAGCUCCAACUA

SEQ ID NO: 24
CUACGUCAUAAGCUCCAAC
```

|                          | SEQ ID NO: 25 |
|--------------------------|---------------|
| CCUACGUCAUAAGCUCCAA      |               |

|                          | SEQ ID NO: 26 |
|--------------------------|---------------|
| GCCUACGUCAUAAGCUCCA      |               |

|                          | SEQ ID NO: 27 |
|--------------------------|---------------|
| UGCCUACGUCAUAAGCUCC      |               |

In some embodiments, one or both of the sense strand and the antisense strand comprises a TT overhang at the 3' end. Thus, in some embodiments, the sense strand comprises a nucleotide sequence that is at least about 80% identical to the nucleotide sequence of any of SEQ ID NOS:10-18, e.g., at least about 80%, 85%, 90%, 91%, 92%, 93%, 94%, 95%, 96%, 97%, 98%, 99%, or more identical to the nucleotide sequence of any of SEQ ID NOS: 10-18. In some embodiments, the nucleotide sequence of the sense strand comprises, consists essentially of, or consist of the nucleotide sequence of any of SEQ ID NOS: 10-18.

|                          | SEQ ID NO: 10 |
|--------------------------|---------------|
| GAGCUUAUGACGUAGGCAAdTdT  |               |

|                          | SEQ ID NO: 11 |
|--------------------------|---------------|
| AGUUGGAGCUUAUGACGUAdTdT  |               |

|                          | SEQ ID NO: 12 |
|--------------------------|---------------|
| GGUAGUUGGAGCUUAUGACdTdT  |               |

|                          | SEQ ID NO: 13 |
|--------------------------|---------------|
| GUAGUUGGAGCUUAUGACGdTdT  |               |

|                          | SEQ ID NO: 14 |
|--------------------------|---------------|
| UAGUUGGAGCUUAUGACGUdTdT  |               |

|                          | SEQ ID NO: 15 |
|--------------------------|---------------|
| GUUGGAGCUUAUGACGUAGdTdT  |               |

|                          | SEQ ID NO: 16 |
|--------------------------|---------------|
| UUGGAGCUUAUGACGUAGGdTdT  |               |

|                          | SEQ ID NO: 17 |
|--------------------------|---------------|
| UGGAGCUUAUGACGUAGGCdTdT  |               |

|                          | SEQ ID NO: 18 |
|--------------------------|---------------|
| GGAGCUUAUGACGUAGGCAdTdT  |               |

In some embodiments, the nucleotide sequence of the antisense strand comprise a nucleotide sequence that is at least about 80% identical to the nucleotide sequence of any of SEQ ID NOS:28-36, e.g., at least about 80%, 85%, 90%, 91%, 92%, 93%, 94%, 95%, 96%, 97%, 98%, 99%, or more identical to the nucleotide sequence of any of SEQ ID NOS: 28-36. In some embodiments, the nucleotide sequence of the antisense strand comprises, consists essentially of, or consist of the nucleotide sequence of any of SEQ ID NOS: 28-36.

|                          | SEQ ID NO: 28 |
|--------------------------|---------------|
| UUGCCUACGUCAUAAGCUCdTdT  |               |

|                          | SEQ ID NO: 29 |
|--------------------------|---------------|
| UACGUCAUAAGCUCCAACUdTdT  |               |

|                          | SEQ ID NO: 30 |
|--------------------------|---------------|
| GUCAUAAGCUCCAACUACCdTdT  |               |

|                          | SEQ ID NO: 31 |
|--------------------------|---------------|
| CGUCAUAAGCUCCAACUACdTdT  |               |

|                          | SEQ ID NO: 32 |
|--------------------------|---------------|
| ACGUCAUAAGCUCCAACUAdTdT  |               |

|                          | SEQ ID NO: 33 |
|--------------------------|---------------|
| CUACGUCAUAAGCUCCAACdTdT  |               |

|                          | SEQ ID NO: 34 |
|--------------------------|---------------|
| CCUACGUCAUAAGCUCCAAdTdT  |               |

|                          | SEQ ID NO: 35 |
|--------------------------|---------------|
| GCCUACGUCAUAAGCUCCAdTdT  |               |

|                          | SEQ ID NO: 36 |
|--------------------------|---------------|
| UGCCUACGUCAUAAGCUCCdTdT  |               |

In some embodiments of this invention, the sense strand of the double stranded RNA molecule can be fully complementary to the antisense strand or the sense strand can be substantially complementary or partially complementary to the antisense strand. By substantially or partially complementary is meant that the sense strand and the antisense strand can be mismatched at about 1, 2, 3, 4, 5, 6, 7, 8, 9, or 10, nucleotide pairings. Such mismatches can be introduced into the sense strand sequence, e.g., near the 3' end, to enhance processing of the double stranded RNA molecule by Dicer, to duplicate a pattern of mismatches in a siRNA molecule inserted into a chimeric nucleic acid molecule or artificial microRNA precursor molecule of this invention, and the like, as would be known to one of skill in the art. Such modification will weaken the base pairing at one end of the duplex and generate strand asymmetry, therefore enhancing the chance of the antisense strand, instead of the sense strand, being processed and silencing the intended gene (Geng and Ding "Double-mismatched siRNAs enhance selective gene silencing of a mutant ALS-causing Allelel" *Acta Pharmacol. Sin.* 29:211-216 (2008); Schwarz et al. "Asymmetry in the assembly of the RNAi enzyme complex" *Cell* 115:199-208 (2003)).

The double stranded RNA molecule of the invention may be in the form of any type of RNA interference molecule known in the art. In some embodiments, the double stranded RNA molecule is a small interfering RNA (siRNA) molecule. In other embodiments, the double stranded RNA molecule is a short hairpin RNA (shRNA) molecule. In other embodiments, the double stranded RNA molecule is part of a microRNA precursor molecule.

The double stranded RNA molecule may be constructed using chemical synthesis and enzymatic ligation reactions by procedures known in the art. For example, a double stranded RNA may be chemically synthesized using naturally occurring nucleotides or various modified nucleotides designed to increase the biological stability of the molecules or to increase the physical stability of the duplex formed between the double stranded RNA and target nucleotide sequences, e.g., phosphorothioate derivatives and acridine substituted nucleotides can be used. Examples of modified nucleotides which can be used to generate the double stranded RNA include, but are not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the double stranded RNA can be produced using an expression vector into which a nucleic acid encoding the double stranded RNA has been cloned.

The double stranded RNA can further include nucleotide sequences wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues can be modified as described. In another non-limiting example, the double stranded RNA is a nucleotide sequence in which one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides can be modified as described. See also, Furdon et al., *Nucleic Acids Res.* 17:9193 (1989); Agrawal et al., *Proc. Natl. Acad. Sci. USA* 87:1401 (1990); Baker et al., *Nucleic Acids Res.* 18:3537 (1990); Sproat et al., *Nucleic Acids Res.* 17:3373 (1989); Walder and Walder, *Proc. Natl. Acad. Sci. USA* 85:5011 (1988); incorporated by reference herein in their entireties for their teaching of methods of making polynucleotide molecules, including those containing modified nucleotide bases).

The invention further relates to a nucleic acid construct comprising the RNA molecule of the invention. The invention further relates to a nucleic acid construct encoding the RNA molecule of the invention and a nucleic acid construct comprising the nucleic acid molecule encoding the RNA molecule. In each of these embodiments, the nucleic acid construct may be a vector or a plasmid, e.g., an expression vector.

Another aspect of the invention relates to a composition comprising the RNA molecule or nucleic acid construct of the invention and another component, e.g., a suitable carrier. In some embodiments, the composition comprises two or more of the RNA molecules or nucleic acid constructs of the invention, wherein the two or more RNA molecules each comprise a different antisense strand. In certain embodiments, the two or more RNA molecules are present on the same nucleic acid construct, on different nucleic acid constructs or any combination thereof. In some embodiments, the composition is a pharmaceutical composition comprising the RNA molecule(s) or nucleic acid construct(s) of the invention and a pharmaceutically acceptable carrier.

It is understood that the compositions of this invention can comprise, consist essentially of or consist of any of the RNA molecules and nucleic acid constructs in any combination and in any ratio relative to one another. Furthermore, by "two or more" is meant 2, 3, 4, 5, 6, 7, 8, 9, 10, etc., up to a total number of RNA molecules and nucleic acid constructs of this invention. In some embodiments, the compositions comprise, consist essentially of or consist of the RNA molecules of SEQ ID NO:1 and SEQ ID NO:3.

In some aspects of the invention, the composition or pharmaceutical composition further comprises additional components that enhance the delivery of the RNA molecule(s) or nucleic acid construct(s) of the invention to a subject, e.g., by enhancing the stability of the RNA molecule(s) or nucleic acid construct(s). In some embodiments, the additional component may be a particle, e.g., a microparticle or nanoparticle. In some embodiments, the particle is a lipid particle, e.g., a liposome, e.g., a microliposome or a nanoliposome. The liposome, microliposome, or nanoliposome may contain any components known in the art to be suitable for preparing liposomes. In some embodiments, the liposome comprises 1,2-dioleoyl-sn-glycero-3-phosphatidylcholine (DOPC). Liposomes may be prepared by methods known in the art, e.g., as described in Pecot et al., *Mol. Cancer Ther.* 13:2876 (2014), incorporated by reference herein in its entirety. In some embodiments, the RNA molecule is formed into a stable nucleic acid lipid particle (SNALP), e.g., using particles such as those provided by Arbutus Biopharma (Doylestown, Pa.). In certain embodiments, the lipid particle comprises, consists essentially of, or consists of cholesterol, 1,2-distearoyl-sn-glycero-3-phosphocholine (DSPC), PEG-cDMA or PEG-cDSA, and 1,2-dilinoleyloxy-3-(N,N-dimethyl)aminopropane (DLinDMA) (see Judge et al., *J. Clin. Invest.* 119:661 (2009)). In some embodiments, the lipid particle comprises two or more of the RNA molecules of the invention, e.g., the RNA molecules of SEQ ID NO:1 and SEQ ID NO:3.

The present invention encompasses cells comprising the RNA molecules and/or nucleic acid constructs of the invention. Thus, in some embodiments, the present invention provides a transformed cell comprising a RNA molecule and/or a nucleic acid construct and/or a composition of this invention, wherein the transformed cell has reduced expression of mutant KRAS as compared to a control cell.

Methods

Various methods are provided herein, employing the nucleic acid molecules, nucleic acid constructs, and/or compositions of this invention. Thus, in one aspect, the present invention provides a method of inhibiting expression of a mutant human KRAS gene comprising one or more of the missense mutations G12C, G12D, G12V, and G13D in a cell, the method comprising contacting the cell with the RNA molecule, nucleic acid construct, composition, and/or pharmaceutical composition of the invention, thereby inhibiting expression of the mutant human KRAS gene in the cell.

Also provided herein is a method of treating cancer in a subject in need thereof, wherein the cancer comprises a mutant human KRAS gene comprising one or more of the missense mutations G12C, G12D, G12V, and G13D, the method comprising delivering to the subject the RNA molecule, nucleic acid construct, composition, and/or pharmaceutical composition of the invention, thereby treating cancer in the subject. A cancer comprising a mutant human KRAS gene comprising one or more of the missense mutations G12C, G12D, G12V, and G13D is a cancer, e.g., a tumor in which one or more cells express the mutant KRAS gene.

In one embodiment of each of these aspects, the subject may be one that has been diagnosed with cancer. In another embodiment, the subject may be one that is at risk of developing cancer (e.g., predisposed due to hereditary factors, smoking, viral infection, exposure to chemicals, etc.). In a further embodiment, the subject may be one that has been identified as carrying a mutant KRAS gene and has or has not been diagnosed with cancer.

The double stranded RNA of the invention can be delivered directly into a cell by any method known in the art, e.g., by transfection or microinjection, e.g., as part of a composition comprising lipid particles. In other embodiments, the double stranded RNA can be delivered to a subject in the form of polynucleotides encoding the RNA to produce expression of the double stranded RNA within the cells of the subject. Those skilled in the art will appreciate that the isolated polynucleotides encoding the RNAs of the invention will typically be associated with appropriate expression control sequences, e.g., transcription/translation control signals and polyadenylation signals.

It will further be appreciated that a variety of promoter/enhancer elements can be used depending on the level and tissue-specific expression desired. The promoter can be constitutive or inducible, depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

To illustrate, the RNA coding sequence can be operatively associated with a cytomegalovirus (CMV) major immediate-early promoter, an albumin promoter, an Elongation Factor 1-α (EF1-α) promoter, a PγK promoter, a MFG promoter, or a Rous sarcoma virus promoter.

Inducible promoter/enhancer elements include hormone-inducible and metal-inducible elements, and other promoters regulated by exogenously supplied compounds, including without limitation, the Zinc-inducible metallothionein (MT) promoter; the dexamethasone (Dex)-inducible mouse mammary tumor virus (MMTV) promoter; the T7 polymerase promoter system (see WO 98/10088); the ecdysone insect promoter (No et al., *Proc. Natl. Acad. Sci. USA* 93:3346 (1996)); the tetracycline-repressible system (Gossen et al., *Proc. Natl. Acad. Sci. USA* 89:5547 (1992)); the tetracycline-inducible system (Gossen et al., *Science* 268:1766 (1995); see also Harvey et al., *Curr. Opin. Chem. Biol.* 2:512 (1998)); the RU486-inducible system (Wang et al., *Nat. Biotech.* 15:239 (1997); Wang et al., *Gene Ther.*, 4:432 (1997)); and the rapamycin-inducible system (Magari et al., *J. Clin. Invest.* 100:2865 (1997)).

Other tissue-specific promoters or regulatory promoters include, but are not limited to, promoters that typically confer tissue-specificity in neurons. These include, but are not limited to, promoters for synapsin 1, tubulin α1, platelet-derived growth factor B-chain, tyrosine hydroxylase, neuron-specific enolase, and neurofilaments. Skeletal muscle cell promoters include, but are not limited to, promoters for β-actin, Pitx3, creatine kinase, and myosin light chain. Cardiac muscle cell promoters include, but are not limited to, promoters for cardiac actin, cardiac troponin T, troponin C, myosin light chain-2, and α-myosin heavy chain. Islet (beta) cell promoters include, but are not limited to, glucokinase, gastrin, insulin, and islet amyloid polypeptide.

Moreover, specific initiation signals are generally required for efficient translation of inserted RNA coding sequences. These translational control sequences, which can include the ATG initiation codon and adjacent sequences, can be of a variety of origins, both natural and synthetic.

The isolated nucleic acid encoding the double stranded RNA can be incorporated into an expression vector. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a double stranded RNA operatively associated with the promoter, and, optionally, a termination sequence including a stop signal for RNA polymerase and a polyadenylation signal for polyadenylase.

Non-limiting examples of animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, baculovirus IE1 promoter, elongation factor 1 alpha (EF1) promoter, phosphoglycerate kinase (PGK) promoter, ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), and pathogenesis and/or disease-related promoters. In addition, any of these expression sequences of this invention can be modified by addition of enhancer and/or regulatory sequences and the like.

Enhancers that may be used in embodiments of the invention include but are not limited to: an SV40 enhancer, a cytomegalovirus (CMV) enhancer, an elongation factor I (EF1) enhancer, yeast enhancers, viral gene enhancers, and the like.

Termination control regions, i.e., terminator or polyadenylation sequences, may be derived from various genes native to the preferred hosts. In some embodiments of the invention, the termination control region may comprise or be derived from a synthetic sequence, a synthetic polyadenylation signal, an SV40 late polyadenylation signal, an SV40 polyadenylation signal, a bovine growth hormone (BGH) polyadenylation signal, viral terminator sequences, or the like.

It will be apparent to those skilled in the art that any suitable vector can be used to deliver the polynucleotide to a cell or subject. The vector can be delivered to cells in vivo. In other embodiments, the vector can be delivered to cells ex vivo, and then cells containing the vector are delivered to the subject. The choice of delivery vector can be made based on a number of factors known in the art, including age and species of the target host, in vitro versus in vivo delivery, level and persistence of expression desired, intended purpose (e.g., for therapy or screening), the target cell or organ, route of delivery, size of the isolated polynucleotide, safety concerns, and the like.

Suitable vectors include, but are not limited to, plasmid vectors, viral vectors (e.g., retrovirus, alphavirus; vaccinia virus; adenovirus, adeno-associated virus and other parvoviruses, lentivirus, poxvirus, or herpes simplex virus), lipid vectors, poly-lysine vectors, synthetic polyamino polymer vectors, and the like.

Any viral vector that is known in the art can be used in the present invention. Protocols for producing recombinant viral vectors and for using viral vectors for nucleic acid delivery can be found in Ausubel et al., Current Protocols in Molecular Biology (Green Publishing Associates, Inc. and John Wiley & Sons, Inc., New York) and other standard laboratory manuals (e.g., Vectors for Gene Therapy. In: *Current Protocols in Human Genetics*. John Wiley and Sons, Inc.: 1997).

Non-viral transfer methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, poly-lysine conjugates, and artificial viral envelopes.

In particular embodiments, plasmid vectors are used in the practice of the present invention. For example, naked plasmids can be introduced into muscle cells by injection into the tissue. Expression can extend over many months, although the number of positive cells is typically low (Wolff et al., Science 247:247 (1989)). Cationic lipids have been demonstrated to aid in introduction of nucleic acids into some cells in culture (Felgner and Ringold, Nature 337:387 (1989)). Injection of cationic lipid plasmid DNA complexes into the circulation of mice has been shown to result in expression of the DNA in lung (Brigham et al., Am. J. Med. Sci. 298:278 (1989)). One advantage of plasmid DNA is that it can be introduced into non-replicating cells.

In a representative embodiment, a nucleic acid molecule (e.g., a plasmid) can be entrapped in a lipid particle bearing positive charges on its surface and, optionally, tagged with antibodies against cell surface antigens of the target tissue (Mizuno et al., No Shinkei Geka 20:547 (1992); PCT publication WO 91/06309; Japanese patent application 1047381; and European patent publication EP-A-43075).

Liposomes that consist of amphiphilic cationic molecules are useful as non-viral vectors for nucleic acid delivery in vitro and in vivo (reviewed in Crystal, Science 270:404 (1995); Blaese et al., Cancer Gene Ther. 2:291 (1995); Behr et al., Bioconjugate Chem. 5:382 (1994); Remy et al., Bioconjugate Chem. 5:647 (1994); and Gao et al., Gene Therapy 2:710 (1995)). The positively charged liposomes are believed to complex with negatively charged nucleic acids via electrostatic interactions to form lipid:nucleic acid complexes. The lipid:nucleic acid complexes have several advantages as nucleic acid transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Feigner et al., Proc. Natl. Acad. Sci. USA 84:7413 (1987); Loeffler et al., Meth. Enzymol. 217:599 (1993); Feigner et al., J. Biol. Chem. 269:2550 (1994)).

Several groups have reported the use of amphiphilic cationic lipid:nucleic acid complexes for in vivo transfection both in animals and in humans (reviewed in Gao et al., Gene Therapy 2:710 (1995); Zhu et al., Science 261:209 (1993); and Thierry et al., Proc. Natl. Acad. Sci. USA 92:9742 (1995)). U.S. Pat. No. 6,410,049 describes a method of preparing cationic lipid:nucleic acid complexes that have a prolonged shelf life.

Nuclear localization signals can also be used to enhance the targeting of the double stranded RNA or expression vector into the proximity of the nucleus and/or its entry into the nucleus. Such nuclear localization signals can be a protein or a peptide such as the SV40 large Tag NLS or the nucleoplasmin NLS. These nuclear localization signals interact with a variety of nuclear transport factors such as the NLS receptor (karyopherin alpha) which then interacts with karyopherin beta.

Expression vectors can be designed for expression of stranded RNA in prokaryotic or eukaryotic cells. For example, stranded RNA can be expressed in bacterial cells such as E. coli, insect cells (e.g., the baculovirus expression system), yeast cells, plant cells or mammalian cells. Some suitable host cells are discussed further in Goeddel, Gene Expression Technology: Methods in Enzymology 185, Academic Press, San Diego, Calif. (1990). Examples of bacterial vectors include, but are not limited to, pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, and pRIT5 (Pharmacia). Examples of vectors for expression in the yeast S. cerevisiae include pYepSecl (Baldari et al., EMBO J. 6:229 (1987)), pMFa (Kurj an and Herskowitz, Cell 30:933 (1982)), pJRY88 (Schultz et al., Gene 54:113 (1987)), and pYES2 (Invitrogen Corporation, San Diego, Calif.). Non-limiting examples of baculovirus vectors available for expression of nucleic acids to produce proteins in cultured insect cells (e.g., Sf 9 cells) include the pAc series (Smith et al., Mol. Cell. Biol. 3:2156 (1983)) and the pVL series (Lucklow and Summers Virology 170:31 (1989)).

Examples of mammalian expression vectors include pWLNEO, pSV2CAT, pOG44, pXT1, pSG (Stratagene) pSVK3, PBPV, pMSG, PSVL (Pharmacia), pCDM8 (Seed, Nature 329:840 (1987)) and pMT2PC (Kaufman et al., EMBO J. 6:187 (1987)). When used in mammalian cells, the expression vector's control functions are often provided by viral regulatory elements. For example, commonly used promoters are derived from polyoma, adenovirus 2, cytomegalovirus and Simian Virus 40.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-limiting examples of non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

In addition to the regulatory control sequences discussed above, the recombinant expression vector can contain additional nucleotide sequences. For example, the recombinant expression vector can encode a selectable marker gene to identify host cells that have incorporated the vector.

Vector DNA can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA and RNA) into a host cell, including, but are not limited to, calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al., Molecular Cloning: A Laboratory Manual 2nd Ed. (Cold Spring Harbor, N.Y., 1989), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

In one embodiment, the double stranded RNA of the invention is administered directly to the subject. Generally, the compounds of the invention will be suspended in a pharmaceutically-acceptable carrier (e.g., physiological saline) and administered orally, topically, or by intravenous infusion, or injected subcutaneously, intramuscularly, intracranially, intrathecally, intraperitoneally, intrarectally, intravaginally, intranasally, intragastrically, intratracheally, or intrapulmonarily. They are preferably delivered directly to the site of the disease or disorder, such as the lung, intestine, or pancreas. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100.0 µg/kg. Wide variations in the needed dosage are to be expected in view of the differing efficiencies of various routes of administration. For example, oral administration would be expected to require higher dosages than administration by i.v. injection (e.g., 2-, 3-, 4-, 6-, 8-, 10-; 20-, 50-, 100-, 150-, or more fold). Variations in these dosage levels can be adjusted using standard empirical routines for optimization as is well understood in the art. Administrations can be single or multiple. Encapsulation of the inhibitor in a suitable delivery vehicle (e.g., polymeric microparticles or implantable devices) may increase the efficiency of delivery, particularly for oral delivery.

According to certain embodiments, the double stranded RNA can be targeted to specific cells or tissues in vivo. Targeting delivery vehicles, including liposomes and viral vector systems are known in the art. For example, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., *Biochemistry* 25:5500 (1986); Ho et al., *J. Biol. Chem.* 262:13979 (1987); Ho et al., *J. Biol. Chem.* 262:13973 (1987); and U.S. Pat. No. 4,957,735 to Huang et al., each of which is incorporated herein by reference in its entirety). Enveloped viral vectors can be modified to deliver a nucleic acid molecule to a target cell by modifying or substituting an envelope protein such that the virus infects a specific cell type. In adenoviral vectors, the gene encoding the attachment fibers can be modified to encode a protein domain that binds to a cell-specific receptor. Herpesvirus vectors naturally target the cells of the central and peripheral nervous system. Alternatively, the route of administration can be used to target a specific cell or tissue. For example, intracoronary administration of an adenoviral vector has been shown to be effective for the delivery of a gene to cardiac myocytes (Maurice et al., *J. Clin. Invest.* 104:21 (1999)). Intravenous delivery of cholesterol-containing cationic liposomes has been shown to preferentially target pulmonary tissues (Liu et al., *Nature Biotechnol.* 15:167 (1997)), and effectively mediate transfer and expression of genes in vivo. Other examples of successful targeted in vivo delivery of nucleic acid molecules are known in the art. Finally, a recombinant nucleic acid molecule can be selectively (i.e., preferentially, substantially exclusively) expressed in a target cell by selecting a transcription control sequence, and preferably, a promoter, which is selectively induced in the target cell and remains substantially inactive in non-target cells.

The double stranded RNA of the present invention can optionally be delivered in conjunction with other therapeutic agents. The additional therapeutic agents can be delivered concurrently with the double stranded RNA of the invention. As used herein, the word "concurrently" means sufficiently close in time to produce a combined effect (that is, concurrently can be simultaneously, or it can be two or more events occurring within a short time period before or after each other). In one embodiment, the double stranded RNA of the invention are administered in conjunction with agents useful for treating cancer, such as: 1) *vinca* alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide). In another embodiment, the compounds of the invention are administered in conjunction with anti-angiogenesis agents, such as antibodies to VEGF (e.g., bevacizumab (AVASTIN), ranibizumab (LUCENTIS)) and other promoters of angiogenesis (e.g., bFGF, angiopoietin-1), antibodies to alpha-v/beta-3 vascular integrin (e.g., VITAXIN), angiostatin, endostatin, dalteparin, ABT-510, CNGRC peptide TNF alpha conjugate, cyclophosphamide, combretastatin A4 phosphate, dimethylxanthenone acetic acid, docetaxel, lenalidomide, enzastaurin, paclitaxel, paclitaxel albumin-stabilized nanoparticle formulation (Abraxane), soy isoflavone (Genistein), tamoxifen citrate, thalidomide, ADH-1 (EXHERIN), AG-013736, AMG-706, AZD2171, sorafenib tosylate, BMS-582664, CHIR-265, pazopanib, P1-88, vatalanib, everolimus, suramin, sunitinib malate, XL184, ZD6474, ATN-161, cilenigtide, and celecoxib, or any combination thereof.

The term "cancer," as used herein, refers to any benign or malignant abnormal growth of cells. Examples include, without limitation, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiments, the cancer is selected from the group of tumor-forming cancers.

Pharmaceutical Compositions

As a further aspect, the invention provides pharmaceutical formulations and methods of administering the same to achieve any of the therapeutic effects (e.g., treatment of cancer) discussed above. The pharmaceutical formulation may comprise any of the reagents discussed above in a pharmaceutically acceptable carrier.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The double stranded RNA or nucleic acid construct of the invention can be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the double stranded RNA (including the physiologically acceptable salts thereof) is typically admixed with, inter alia, an acceptable carrier. The carrier can be a solid or a liquid, or both, and is preferably formulated with the double stranded RNA as a unit-dose formulation, for example, a tablet, which can contain from 0.01 or 0.5% to 95% or 99% by weight of the double stranded RNA. One or more double stranded RNAs can be incorporated in the formulations of the invention, which can be prepared by any of the well-known techniques of pharmacy.

A further aspect of the invention is a method of treating subjects in vivo, comprising administering to a subject a pharmaceutical composition comprising a double stranded RNA of the invention in a pharmaceutically acceptable carrier, wherein the pharmaceutical composition is administered in a therapeutically effective amount. Administration of the double stranded RNA of the present invention to a human subject or an animal in need thereof can be by any means known in the art for administering compounds.

Non-limiting examples of formulations of the invention include those suitable for oral, rectal, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intracranial, intrathecal, and inhalation administration, administration to the liver by intraportal delivery, as well as direct organ injection (e.g., into the liver, into a limb, into the brain or spinal cord for delivery to the central nervous system, into the pancreas, or into a tumor or the tissue surrounding a tumor). The most suitable route in any given case will depend on the nature and severity of the condition being treated and on the nature of the particular compound which is being used. In some embodiments, it may be desirable to deliver the formulation locally to avoid any side effects associated with systemic administration. For example, local administration can be accomplished by direct injection at the desired treatment site, by introduction intravenously at a site near a desired treatment site (e.g., into a vessel that feeds a treatment site). In some embodiments, the formulation can be delivered locally to ischemic tissue. In certain embodiments, the formulation can be a slow release formulation, e.g., in the form of a slow release depot.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the compound. Suitable formulations comprise citrate or bis\tris buffer (pH 6) or ethanol/water and contain from 0.1 to 0.2M of the compound.

The compound can alternatively be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the compound in a local rather than systemic manner, for example, in a depot or sustained-release formulation.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the compounds disclosed herein or salts thereof, can be lyophilized to produce a lyophilizate which can be reconstituted with a pharmaceutically acceptable carrier, such as water, to regenerate a liposomal suspension.

In the case of water-insoluble compounds, a pharmaceutical composition can be prepared containing the water-insoluble compound, such as for example, in an aqueous base emulsion. In such an instance, the composition will contain a sufficient amount of pharmaceutically acceptable emulsifying agent to emulsify the desired amount of the compound. Particularly useful emulsifying agents include phosphatidyl cholines and lecithin.

In particular embodiments, the compound is administered to the subject in a therapeutically effective amount, as that term is defined above. Dosages of pharmaceutically active compounds can be determined by methods known in the art, see, e.g., *Remington's Pharmaceutical Sciences* (Maack Publishing Co., Easton, Pa.). The therapeutically effective dosage of any specific compound will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the compound, including the cases where a salt is employed. Toxicity concerns at the higher level can restrict intravenous dosages to a lower level such as up to about 10 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 μmol/kg to 50 μmol/kg, and more particularly to about 22 μmol/kg and to 33 μmol/kg of the compound for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults. In other embodiments, the subject is an animal model of cancer. In certain embodiments, the subject has or is at risk for cancer.

The following examples are not intended to limit the scope of the claims to the invention, but are rather intended to be exemplary of certain embodiments. Any variations in the exemplified methods that occur to the skilled artisan are intended to fall within the scope of the present invention. As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or

Example 1

Mutant KRAS-Specific siRNAs

Methods:

Novel mutant-specific siRNAs (MS siRNAs) were designed based on previous literature that suggests a 3-mismatch tolerance threshold for 19-nucleotide siRNA efficacy (Naito et al., *Nucleic Acids Res.* 32:W124 (2004)). With two or fewer mismatches between the sequence and the target gene, the siRNA is able to successfully bind and knockdown expression of the gene of interest; however, at and above the 3 mismatch threshold, the siRNA fails to recognize the target, thus allowing for expression of the encoded protein. Custom MS siRNAs were generated using open source softwares provided by Sigma Aldrich, Life Technologies and Dharmacon to be antisense to an artificial, hyper-mutated version of the WT KRAS gene which never actually occurs in nature, with exactly 3 point mutations corresponding to each of the most commonly occurring KRAS mutants (G12C, G12D or G12V, and G13D). Thirty flanking nucleotides were included upstream and downstream of these sites in the artificial, hyper-mutated mRNA input (FIG. 1). Of note, siRNA sequences were designed to target two different artificial mRNA sequences; one that simultaneously contained specific missense mutations in codons 12 (G12C and G12D) and 13 (G13D), and another that simultaneously contained specific missense mutations in codons 12 (G12C and G12V) and 13 (G13D) (FIG. 1). The resultant sequence is thus antisense with 3 mismatch errors to WT KRAS but only 2 mismatch errors to each of the 3 mutant KRAS alleles. Consequently, it was hypothesized that these MS siRNAs will optimize the task of targeting mutant KRAS while sparing the WT KRAS allele since the sequence is below the 3 mismatch threshold for the former and above for the latter. In addition, by introducing one mutation from each of 3 different prevalent KRAS mutants in the custom sequence design, the resultant siRNA has the added potential benefit of simultaneously targeting several KRAS mutants rather than one.

Constructs containing the WT, G12C, G12D, G12V, or G13D KRAS gene inserted into pBABE-puro retroviral expression vectors were prepared. To expand the vector constructs, plasmids were added to high efficiency competent *E. coli* cells and incubated in S.O.C. media on a shaker at 37° C. Cells were then plated on ampicillin agarose plates and incubated at 37° C. overnight. Liquid cultures were prepared by picking and placing bacterial colonies from the overnight plates into LB broth with 1 µl/ml carbocyclin and incubating overnight on a shaker at 37° C. Liquid cultures were performed in triplicate. Plasmid DNA from the resultant turbid cultures was purified using a QIAprep Spin Miniprep Kit (Qiagen). Successful plasmid expansion was confirmed via restriction enzyme digest using BamHI and HindIII and gel electrophoresis. Undigested plasmids from the Miniprep were further expanded in LB Broth with 0.1 µl/ml carbocyclin and then purified using a QIAprep Spin Maxiprep Kit (Qiagen).

To produce retrovirus containing the pBABE-puro-KRAS plasmids, $9\times10^6$ HEK 293T cells were seeded onto 6 cm cell culture plates in 293T media (DMEM with 10% FBS and 1% penicillin-streptomycin) and incubated at 37° C., 5% $CO_2$. After 24 hours, plasmid DNA mixtures were prepared for each pBABE-puro-KRAS plasmid by creating a mixture of 0.01 µg/µl plasmid construct and 0.01 µg/µl PCL10A pack vector plasmid to OptiMEM media. In addition, a L2K mixture was prepared by adding 0.05 µg/µl Lipofectamine 2000 (Thermo Fisher Scientific) in OptiMEM media and incubating at room temperature for 5 minutes. The L2K mixture was then combined 1:1 with each plasmid DNA mixture and incubated at room temperature for 20 minutes. Media was removed from the incubated cells, then 2 ml of 293T media was added to each well along with 250 µl of the plasmid DNA/L2K mixture. After another 24 hours, the plasmid DNA/L2K media was replaced with 293T media. After another 24 hours, the resultant viral media was collected from the wells and replaced with fresh 293T media. Virus media was stored overnight on ice at 4° C. After another 24 hours, media was collected again from the wells and added to the previously stored virus. The mixture was centrifuged at room temperature, then the supernatant was collected. This process was repeated using mCherry and 293T media instead of plasmid construct to produce mCherry and empty vector virus, respectively.

To infect cells with KRAS plasmid, NIH 3T3 cells were harvested and seeded at 100,000 per well in 6 well plates in complete media (DMEM with 10% Colorado calf serum and 1% pen/strep). After 4-6 hours and once the cells attached, the media was aspirated and 2 ml of complete media with 10 µl/ml polybrene along with 250 µl of viral media (WT, G12C, G12D, G12V, G13D, mCherry, and empty vector) or complete media (negative controls) were added to each well. Cells were centrifuged at 1500 g for 60 minutes at 30° C., then incubated overnight at 37° C. After 24 hours, wells were aspirated and complete media was added to each well. After another 24 hours, wells were aspirated and complete media with 2 µg/ml puromycin was added. Media was replaced with puromycin media every 24 hours until no living cells remained in the negative control wells. Successful infection was further verified using mCherry expression.

RNAi knockdown was induced in KRAS-infected NIH 3T3 cells plated at a density of 60,000 cells per 500 µl complete media per well in 24 well plates. Sequences for the scrambled control siRNA, as well as positive controls (Seq #2 and #3, G12C and G12D siRNAs) previously found to potently silence wild-type and mutant KRAS were used as indicated in FIG. 1 (Fleming et al., *Mol. Cancer Res.* 3:413 (2005); Pecot et al., *Mol. Cancer Ther.* 13:2876 (2014)). Cells were incubated in 5:1 mixture of complete media and serum-free media, along with 20 nM siRNA (Sigma Aldrich) and Lipofectamine® RNAiMAX transfection reagent (Thermo Fisher Scientific, 2:1 ratio of transfection reagent to siRNA by volume) for 5 hours at 37° C. in 5% $CO_2$. Media was removed, and cells were incubated in complete media only for another 19 hours before RNA was collected and purified using a QIAprep Spin Miniprep Kit.

Purified RNA from siRNA treatments was quantified using a spectrophotometer, then reverse transcribed to cDNA using an iScript™ cDNA Synthesis Kit (Bio-Rad). To quantify relative expression levels of KRAS, RT-PCR reactions were performed by monitoring real-time changes in fluorescent intensity of SYBR green on the StepOnePlus™ Real-Time PCR System (Thermo Fisher Scientific). Each sample was run in triple replicate. The StepOnePlus™ was also used to obtain RQ values using the ΔΔCT analysis to calculate ΔCt values by comparing cycle threshold (Ct values) of KRAS to those of the target reference gene, 18s, then compare ΔCt values for each siRNA to those of the NC siRNA. Error bars represent 1 standard deviation. Data represents the result of one trial of two biological replicates for WT and G12D and two trials of two biological replicates for G12C, G12V, and G13D. Reverse transfection experiments were performed in duplicate for each siRNA for each cell line.

Results:

To test the efficacy of mutant-specific KRAS silencing in vitro, a panel of candidate MS KRAS siRNA sequences was tested for their ability to knock-down KRAS expression in both WT and target mutant KRAS-expressing cells. The 12CD13D_1 sequence was observed to exhibit a sparing of WT KRAS expression (only 4% knock-down compared to negative control siRNA) while knocking down G12C (50%), G12D (82%), and G13D mutant KRAS (66%) (FIG. 2A). The sequence was also unexpectedly noted to knock down G12V expression (58%). Additionally, 12CD13D_2 and 12CD13D_4 were also found to exhibit WT sparing and mutant knockdown. However, the former appeared to exhibit less WT sparing than 12CD13D_1 and the latter less KRAS knockdown in all cell lines (FIG. 2A). The remaining sequences exhibited either low potency against mutant KRAS, high KRAS knockdown in the WT KRAS cell line, or both (FIG. 2A).

Figure 2B:
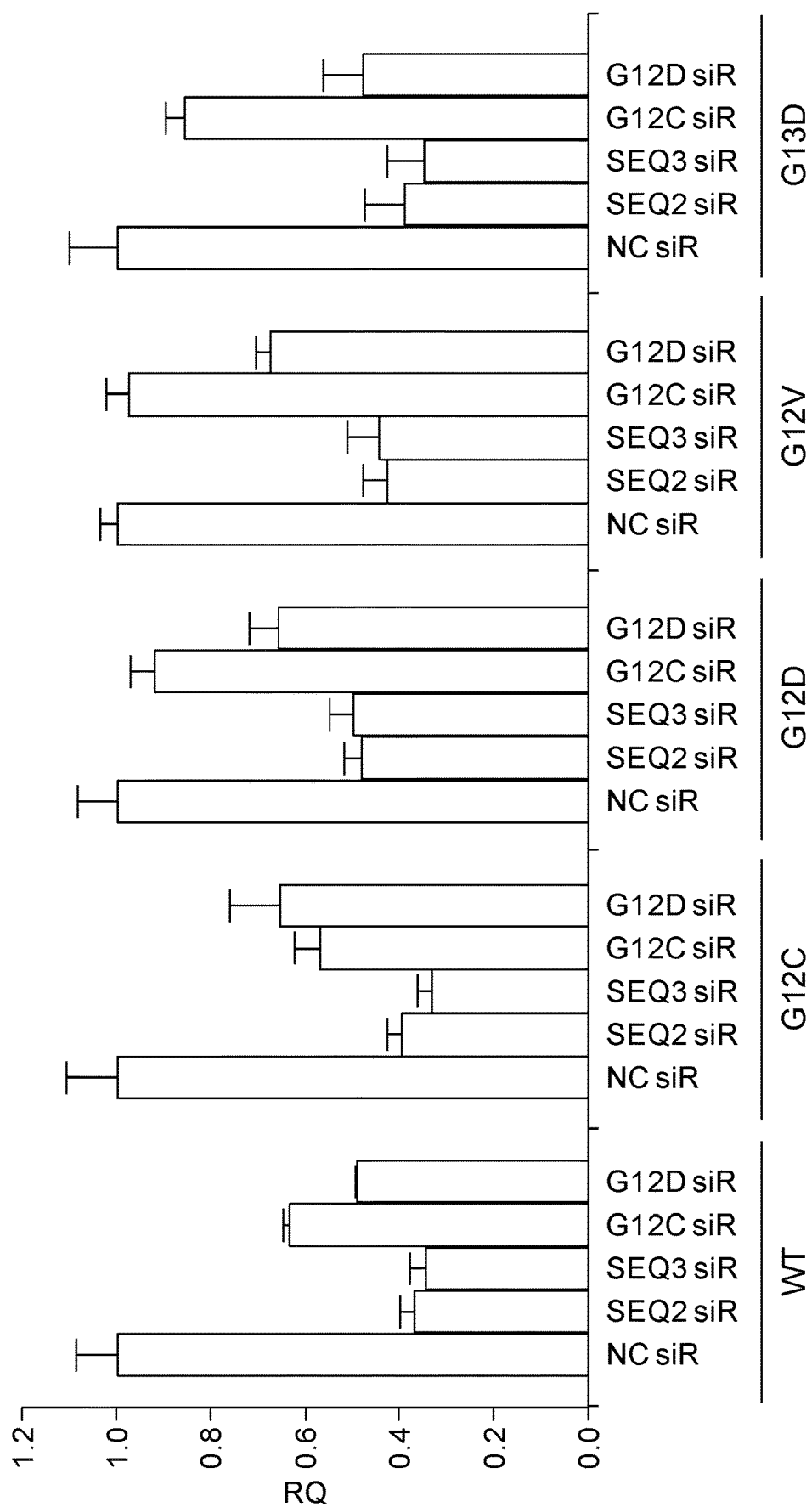

In addition, G12C- and G12D-specific siRNA sequences (Fleming et al., *Mol. Cancer Res.* 3:413 (2005)) were tested in order to compare the efficacy of MS siRNA sequences against those previously demonstrated to exhibit target-specificity. However, the mutant-specificity of these sequences was not confirmed, and the sequences did not exhibit the expected preferential knockdown of G12C and G12D mutant KRAS, respectively, over the WT or other mutant alleles (FIG. 2B).

Figure 3:
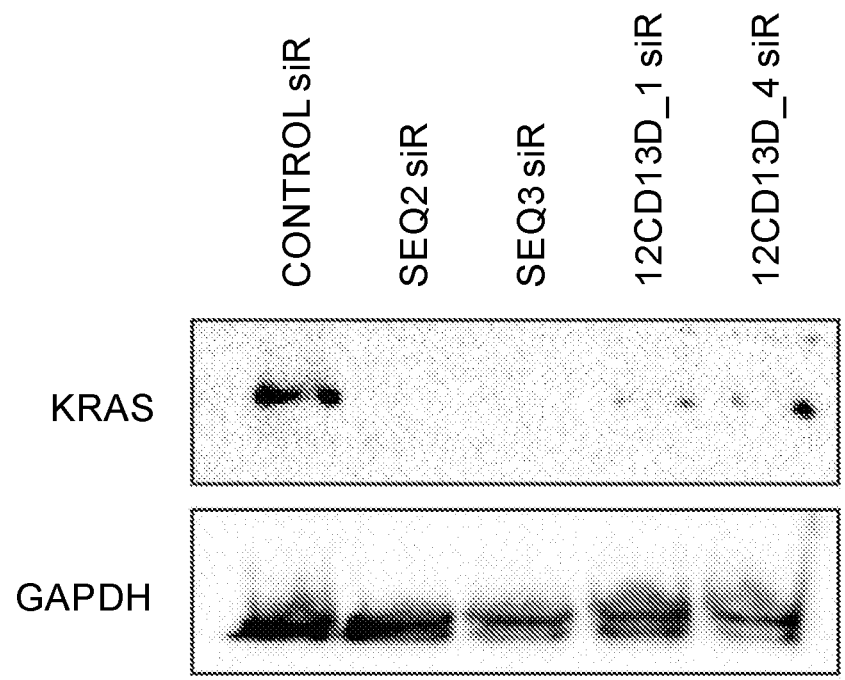
FIG. 3 shows the testing of custom KRAS siRNA sequences 12CD13D_1 and 12CD13D_4 in a KRAS G12D mutant lung cancer cell line.

KRAS siRNA sequences 12CD13D_1 and 12CD13D_4 were tested in a KRAS G12D mutant lung cancer cell line. Using a control siRNA (Scr) and two previously validated KRAS siRNAs (Seq #2 and #3), it was demonstrated that customized, mutant specific KRAS siRNA sequences 12CD13D_1 and 12CD13D_4 are highly effective at silencing KRAS protein expression (FIG. 3).

Testing all possible siRNA sequence permutations between our custom siRNA sequences. In order to verify the best possible custom KRAS siRNA sequences (leading sequences being 12CD13D_1 and 12CD13D_4), a library of sequences (12CD13D_A thru 12CD13D_F) were tested that incrementally move downstream between 12CD13D_1 and 12CD13D_4 (FIG. 4).

Figure 5:
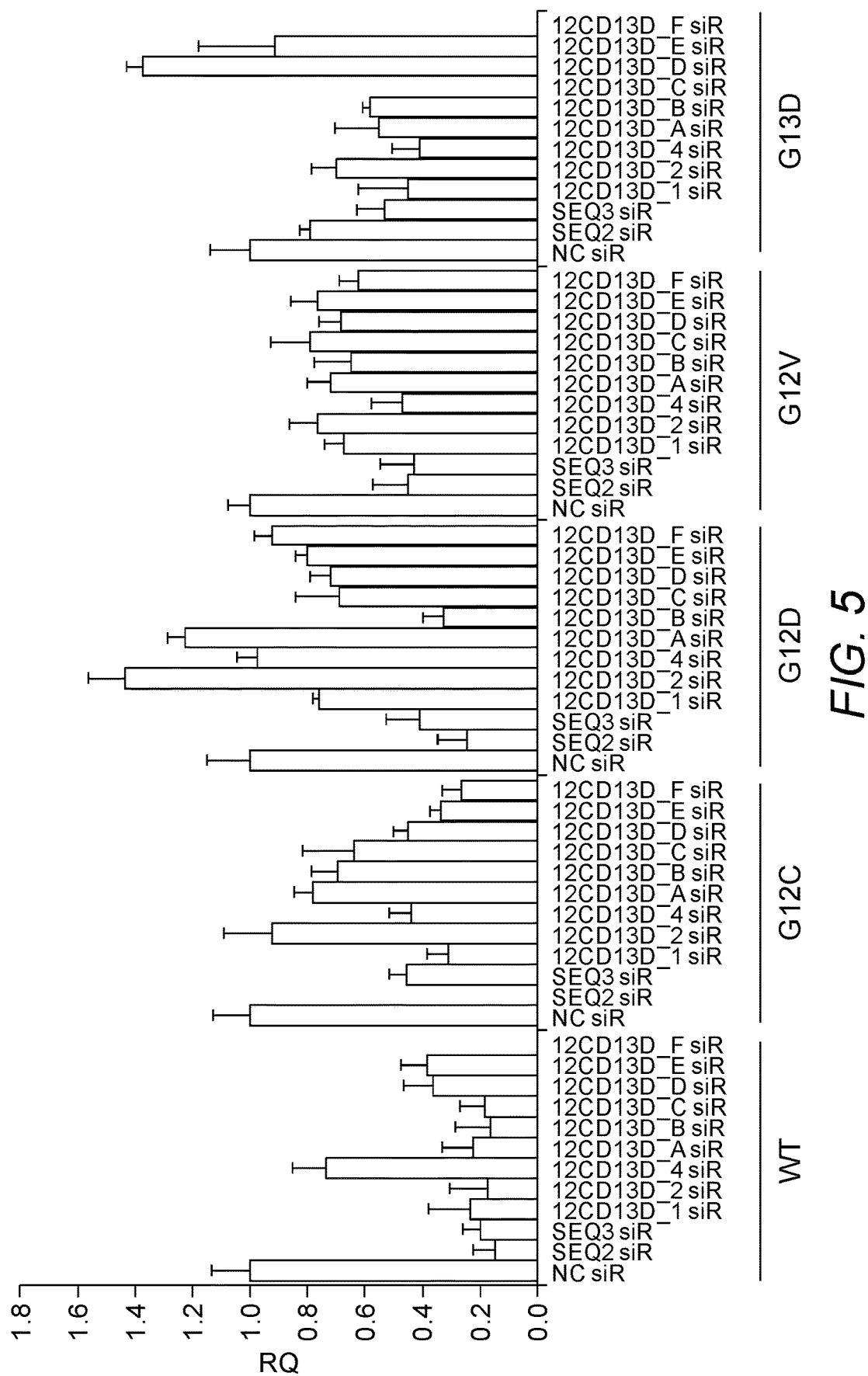
FIG. 5 shows the relative expression of wild-type and mutant KRAS mRNAs in 3T3 cells.

Following stable transduction of 3T3 cells with either wild-type (WT) or mutant G12C, G12D, G12V and G13D human KRAS sequences, the cells were transfected with KRAS siRNA sequences listed in FIG. 5. Twenty-four hours after transfection, cells were lysed, RNA collected and cDNA was made. Quantitative qPCR was performed for KRAS using 18s as a house-keeping gene. It was found that the leading 12CD13D_1 and 12CD13D_4 custom sequences were still the best overall at silencing mutant KRAS, while the other possible KRAS siRNA sequences ("A" thru "F") were less potent overall at silencing the different KRAS mRNA sequences. On this experiment the custom KRAS siRNA 12CD13D_4 sequence was best at sparing the WT sequence.

Discussion:

Although numerous efforts have been made to target mutant KRAS, no direct inhibitors are currently in clinical use. Moreover, most current small-molecule cancer therapeutics exhibit low target specificity, resulting in adverse toxicity in non-cancerous cells (Pecot et al., *Nat. Rev. Cancer* 11:59 (2011)). Despite current headways in inhibiting downstream effectors in the KRAS signaling pathway, KRAS remains an elusive target for drug development (Cox et al., *Nat. Rev. Drug Discov.* 13:828 (2014)). As such, this study investigated the efficacy of novel MS siRNA as a means of selectively inhibiting expression of mutant KRAS.

Based on these preliminary findings, the 12CD13D_1 and 12CD13D_2 siRNA sequences were chosen as lead candidates for further investigation as therapeutic agents because of their high mutant-specificity and potency. To a lesser extent, 12CD13D_4 is also a promising candidate; however, its low efficiency in knocking down KRAS expression in mutant targets suggests that it may not be effective as a clinically relevant therapeutic agent. By contrast, the G12C- and G12D-specific siRNA do not appear to exhibit any sort of sparing of the WT KRAS allele.

In addition, the low specificity of both sequences designed to target the G12V rather than the G12D point mutation suggests a greater tolerance for WT KRAS in G12V-targeting sequences.

These preliminary findings collectively suggest the viability of novel MS siRNAs as a mutant-specific vehicle for silencing oncogenic KRAS. With its potential as an effective payload with mutant KRAS specificity, novel mutant-specific siRNAs present a promising avenue of pursuit for drugging the formerly "undruggable."

All publications, patents, and patent applications are herein incorporated by reference to the same extent as if each individual publication, patent, or patent application was specifically and individually indicated to be incorporated by reference.

Although the foregoing invention has been described in some detail by way of illustration and example for purposes of clarity of understanding, it will be obvious that certain changes and modifications may be practiced within the scope of the list of the foregoing embodiments and the appended claims.

What is claimed is:

1. A double stranded RNA molecule comprising an antisense strand and a sense strand, wherein the nucleotide sequence of the antisense strand is at least 90% complementary to a region of the nucleotide sequence of a synthetic human KRAS gene that contains the missense mutations G12C, G12D, and G13D or the missense mutations G12C, G12V, and G13D, the region consisting essentially of about 18 to about 25 consecutive nucleotides; wherein the double stranded RNA molecule inhibits expression of a mutant human KRAS gene comprising one or more of the missense mutations G12C, G12D, G12V, and G13D and minimally inhibits expression of wild-type human KRAS.

2. The RNA molecule of claim 1, wherein the nucleotide sequence of the antisense strand contains at least 3 mismatches with the nucleotide sequence of wild-type human KRAS.

3. The RNA molecule of claim 1, wherein the nucleotide sequence of the antisense strand contains no more than 2 mismatches with the nucleotide sequence of a mutant human KRAS gene comprising one or more of the missense mutations G12C, G12D, G12V, and G13D.

4. The RNA molecule of claim 1, wherein the nucleotide sequence of the sense strand comprises a nucleotide sequence that is at least 90% identical to the nucleotide sequence of any of SEQ ID NOS: 1-18.

5. The RNA molecule of claim 1, wherein the nucleotide sequence of the sense strand comprises the nucleotide sequence of any of SEQ ID NOS:1-18.

6. The RNA molecule of claim 1, wherein the nucleotide sequence of the antisense strand comprise a nucleotide sequence that is at least 90% identical to the nucleotide sequence of any of SEQ ID NOS:19-36.

7. The RNA molecule of claim 1, wherein the nucleotide sequence of the antisense strand comprises the nucleotide sequence of any of SEQ ID NOS:19-36.

8. The RNA molecule of claim 1, wherein the double stranded RNA molecule is a small interfering RNA (siRNA) molecule.

9. The RNA molecule of claim 1, wherein the double stranded RNA molecule is a short hairpin RNA (shRNA) molecule.

10. A nucleic acid construct comprising the RNA molecule of claim 1.

11. A nucleic acid molecule encoding the RNA molecule of claim 1.

12. A nucleic acid construct comprising the nucleic acid molecule of claim 11.

13. A composition comprising the RNA molecule of claim 1.

14. A composition comprising two or more of the RNA molecules of claim 1, wherein the two or more RNA molecules each comprise a different antisense strand.

15. The composition of claim 14, wherein the two or more RNA molecules are present on the same nucleic acid construct, on different nucleic acid constructs or any combination thereof.

16. The composition of claim 13, further comprising a nanoparticle.

17. The composition of claim 16, wherein the nanoparticle is a nanoliposome.

18. A pharmaceutical composition comprising the RNA molecule of claim 1 and a pharmaceutically acceptable carrier.

19. A method of inhibiting expression of a mutant human KRAS gene comprising one or more of the missense mutations G12C, G12D, G12V, and G13D in a cell, the method comprising contacting the cell with the RNA molecule of claim 1, thereby inhibiting expression of the mutant human KRAS gene in the cell.

20. A method of treating cancer in a subject in need thereof, wherein the cancer comprises a mutant human KRAS gene comprising one or more of the missense mutations G12C, G12D, G12V, and G13D, the method comprising delivering to the subject the RNA molecule of claim 1, thereby treating cancer in the subject.

* * * * *

UNITED STATES PATENT AND TRADEMARK OFFICE
CERTIFICATE OF CORRECTION

Page 1 of 1

PATENT NO. : 10,619,159 B2
APPLICATION NO. : 16/070600
DATED : April 14, 2020
INVENTOR(S) : Pecot et al.

It is certified that error appears in the above-identified patent and that said Letters Patent is hereby corrected as shown below:

On the Title Page

Item (60) Related U.S. Application Data:
Please add -- Related U.S. Application Data
(60) Provisional Application No. 62/280,458, filed on January 19, 2016 --

In the Specification

Column 26, Line 48:
Please correct "P1-88" to read -- PI-88 --

Column 32, Line 62:
Please correct "AACT" to read -- ΔΔCT --

Signed and Sealed this
Sixth Day of October, 2020

Andrei Iancu
*Director of the United States Patent and Trademark Office*